United States Patent
Lebovic et al.

(10) Patent No.: US 9,039,593 B2
(45) Date of Patent: *May 26, 2015

(54) SYSTEMS AND METHODS FOR DELIVERING RADIATION THERAPY

(75) Inventors: Gail S. Lebovic, Pacific Grove, CA (US); George D. Hermann, Portola Valley, CA (US); Douglas S. Sutton, Pacifica, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 943 days.

This patent is subject to a terminal disclaimer.

(21) Appl. No.: 12/395,624

(22) Filed: Feb. 27, 2009

(65) Prior Publication Data
US 2009/0240095 A1 Sep. 24, 2009

Related U.S. Application Data

(60) Provisional application No. 61/067,745, filed on Feb. 29, 2008.

(51) Int. Cl.
*A61M 36/10* (2006.01)
*A61N 5/10* (2006.01)

(52) U.S. Cl.
CPC ....... *A61N 5/1016* (2013.01); *A61N 2005/1004* (2013.01)

(58) Field of Classification Search
CPC ............................ A61N 5/1001–5/102; A61N 2005/1003–2005/10259
USPC ......................................... 600/1–8; 606/2–52
See application file for complete search history.

(56) References Cited

U.S. PATENT DOCUMENTS

| | | | |
|---|---|---|---|
| 4,350,151 A | | 9/1982 | Scott |
| 5,653,683 A | * | 8/1997 | D'Andrea ........................ 604/21 |
| 5,720,717 A | | 2/1998 | D'Andrea |
| 5,863,284 A | * | 1/1999 | Klein ................................ 600/3 |
| 6,050,930 A | | 4/2000 | Teirstein |
| 6,068,608 A | * | 5/2000 | Davis et al. ................... 604/4.01 |
| 6,200,257 B1 | * | 3/2001 | Winkler ............................ 600/3 |
| 6,413,204 B1 | | 7/2002 | Winkler |
| 6,923,754 B2 | * | 8/2005 | Lubock ............................ 600/3 |
| 7,338,430 B2 | | 3/2008 | Lim |
| 7,357,770 B1 | | 4/2008 | Cutrer |

(Continued)

FOREIGN PATENT DOCUMENTS

| | | |
|---|---|---|
| EP | 1681077 | 7/2006 |
| WO | 9962598 | 12/1999 |

(Continued)

OTHER PUBLICATIONS

PCT, International Search Report and Written Opinion in International application No. PCT/US09/35598, Jul. 6, 2009, 13 pages.

(Continued)

*Primary Examiner* — Catherine B Kuhlman
(74) *Attorney, Agent, or Firm* — Houst Consulting

(57) ABSTRACT

Described here are conformable brachytherapy applicators. The conformable brachytherapy applicators generally follow the contour of tissue surfaces so that distances between radiation sources and target tissues can be precisely determined and radiation dose clouds can be readily shaped. Systems and methods for using the conformable brachytherapy applicators are also described.

38 Claims, 12 Drawing Sheets

(56) References Cited

U.S. PATENT DOCUMENTS

| | | |
|---|---|---|
| 7,497,819 B2 | 3/2009 | White et al. |
| 7,497,820 B2 | 3/2009 | White et al. |
| 7,662,082 B2 | 2/2010 | White et al. |
| 8,079,946 B2 * | 12/2011 | Lubock et al. .................. 600/3 |
| 8,465,407 B2 * | 6/2013 | Lebovic et al. .................. 600/6 |
| 8,550,972 B2 * | 10/2013 | Lebovic et al. .................. 600/6 |
| 2003/0216768 A1 | 11/2003 | Gitis |
| 2004/0006305 A1 * | 1/2004 | Hebert et al. ............. 604/96.01 |
| 2004/0087827 A1 * | 5/2004 | Lubock ............................ 600/3 |
| 2005/0080313 A1 * | 4/2005 | Stewart et al. .................. 600/3 |
| 2006/0100475 A1 * | 5/2006 | White et al. ..................... 600/3 |
| 2007/0173680 A1 * | 7/2007 | Rioux et al. ..................... 600/2 |
| 2008/0167514 A1 | 7/2008 | Lim |
| 2008/0214887 A1 | 9/2008 | Heanue |
| 2008/0293994 A1 | 11/2008 | Francescatti |
| 2008/0300445 A1 | 12/2008 | Francescatti |
| 2009/0156882 A1 | 6/2009 | Sing |
| 2009/0234176 A1 | 9/2009 | Lebovic et al. |
| 2009/0234177 A1 | 9/2009 | Lebovic et al. |
| 2009/0234178 A1 | 9/2009 | Lebovic et al. |
| 2009/0240095 A1 | 9/2009 | Lebovic et al. |
| 2009/0264696 A1 | 10/2009 | White et al. |
| 2009/0312593 A1 | 12/2009 | Drobnik |
| 2010/0121129 A1 | 5/2010 | White et al. |
| 2010/0130807 A1 | 5/2010 | White et al. |
| 2010/0152519 A1 | 6/2010 | White et al. |
| 2010/0222628 A1 | 9/2010 | White et al. |
| 2011/0257459 A1 | 10/2011 | Sutton et al. |

FOREIGN PATENT DOCUMENTS

| | | | |
|---|---|---|---|
| WO | WO 2006074879 A1 * | 7/2006 | ............... A61N 5/10 |
| WO | 2007079278 | 7/2007 | |
| WO | 2008112223 | 9/2008 | |

OTHER PUBLICATIONS

PCT, International Search Report in International application No. PCT/US11/24587, Apr. 6, 2011, 1 page.

Nag et al., "The American Brachytherapy Society Recommendations for Low-Dose-Rate Brachytherapy for Carcinoma of the Cervix," Int. J. Radiation Oncology Biol. Phys., 2002, vol. 52(1), pp. 33-48.

Small et al., "American Brachytherapy Society Survey Regarding Practice Patterns of Postoperative Irradiation for Endometrial Cancer: Current Status of Vaginal Brachytherapy," Int. J. Radiation Oncology Biol. Phys., 2005, vol. 63(5), pp. 1502-1507.

Yoo et al., "Treatment planning for prostate brachytherapy using region of interest adjoint functions and a greedy heuristic," Phys. Med. Biol. 2003, No. 48, pp. 4077-4090.

* cited by examiner

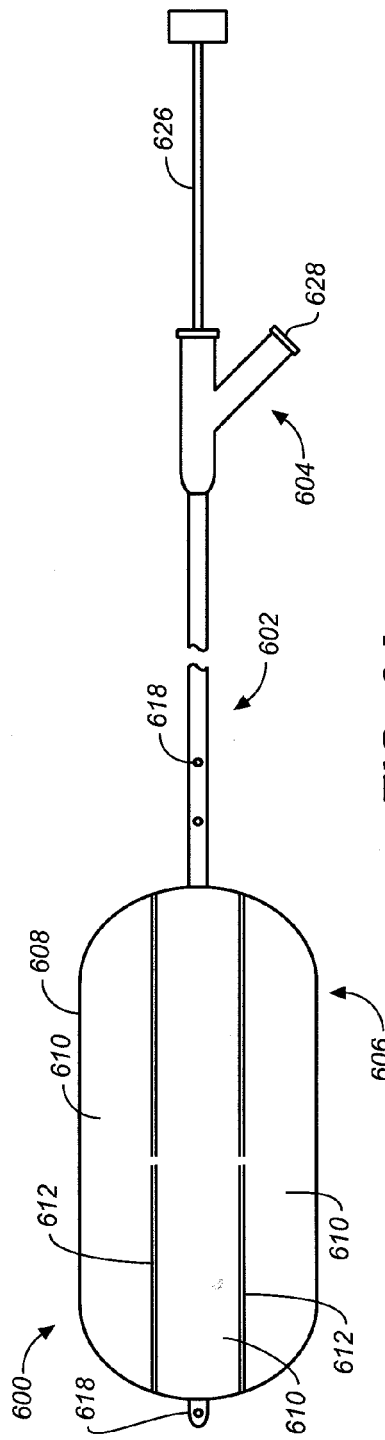

SYSTEMS AND METHODS FOR DELIVERING RADIATION THERAPY

CROSS-REFERENCE TO RELATED APPLICATIONS

This application claims priority to U.S. Provisional Application Ser. No. 61/067,745 filed on Feb. 29, 2008, which is hereby incorporated by reference in its entirety.

FIELD

Described here are conformable brachytherapy applicators. Specifically, brachytherapy applicators that conform to various gynecological tissues are described. Systems and methods for delivering radiation therapy using the brachytherapy applicators are also described.

BACKGROUND

Radiation therapy is used to treat various malignant tumors, either preoperatively, as adjuvant therapy after surgery, as primary therapy for patients unable to tolerate surgery, or to treat recurrences after surgery. Patients undergoing radiation therapy may receive external beam treatment, brachytherapy, or both. Brachytherapy is a term used to describe the short distance treatment of cancer with radiation. This type of treatment typically involves placing the radiation directly into or near the tissue to be treated. The radiation dose may then be delivered over a short period of time (temporary implants) or over the lifetime of the source to a complete decay (permanent implants).

Brachytherapy may be divided into two main classes: intracavitary and interstitial. With intracavitary brachytherapy, the radiation sources are placed within a body cavity close to the affected tissue. In interstitial brachytherapy, the radiation sources are implanted within a volume of tissue. Positioning of the radiation sources is an important aspect of brachytherapy. In order to effectively deliver radiation to the target tissue while helping to minimize exposure (and radiation damage) of surrounding healthy or normal tissue, the radiation sources must be properly positioned during the entire course of treatment.

Various types of brachytherapy applicators have been developed for delivering radiation. In the gynecologic field, an exemplary development was the Fletcher-Suit cervical applicator. This applicator consists of a central tube (tandem) and lateral capsules (ovoids or colpostats). The lateral colpostats provide intravaginal positioning while the central tandem traverses the vaginal canal to project into the cervix. Although the Fletcher-Suit applicator has been widely used, maintaining its position in situ can be difficult due to their weight and the difficulty of ensuring a secure connection between the colpostats and tandem. Other brachytherapy applicators have been developed, e.g., the Miami Vaginal Applicator (Nucletron BV, Veenendaal, NL). However, they can be uncomfortable and/or difficult to insert due to their rigidity and incapability of accommodating variations in anatomy, e.g., variations in the size, shape, and orientation of the uterus among patients, or postoperative distortions in anatomy.

Given the importance of brachytherapy in the treatment of cancer, brachytherapy applicators having physical and/or functional characteristics that help optimize radiation delivery to target tissues while minimizing exposure to healthy or normal tissues would be useful. Applicators that can be easily and securely positioned within the body would be desirable. Additional applicator designs, e.g., applicators capable of conforming to tissue surfaces and accommodating variations in anatomy would also be useful.

SUMMARY

Described here are conformable brachytherapy applicators, and systems and methods for using them to deliver radiation therapy. The conformable nature of the applicators may enable shaping of dose clouds that help maximize the amount of radiation delivered to target tissues while helping to minimize the amount of radiation delivered to healthy or normal tissues. The applicators may be useful in various locations within the body, e.g., natural or surgically created cavities or spaces, to treat many different types of proliferative conditions, including malignancies. For example, the applicators may be used to deliver radiation to anal/rectal/pelvic tissues, abdominal tissues, or tissues of the head and neck region. Use of the applicators to deliver radiation to gynecologic tissues may be beneficial. The applicators may also be used with various imaging modalities. For example, they may be imageable by x-ray, computed tomography, and magnetic resonance imaging modalities. In some variations, the applicator is housed within a sheath and a removable handle. The applicators may be pre-packaged within the sheath and/or removable handle, or placed within the sheath and/or removable handle immediately prior to use during a brachytherapy procedure.

The brachytherapy applicators generally include an elongate body having a central lumen and at least one peripheral lumen, each of which extends at least partially through the elongate body. It should be understood that the term "lumen" refers to any passage through which a radiation source may be advanced. For example, a lumen may refer to a space defined by a catheter or conduit, the catheter or conduit itself, or a combination thereof, or a predefined space created within the elongate body without the use of a catheter, e.g., a hole that extends along the long axis of the elongate body. The lumens may have any suitable configuration. For example, the lumens may be circular, half-circular, spherical, etc.

The elongate body may have an initial expanded configuration, an unexpanded configuration for advancement of the applicator to a target tissue, and an expanded deployed configuration. In some variations, the initial expanded configuration refers to the configuration of the elongate body immediately prior to insertion into the body and in its natural state, e.g., a state where the elongate body or applicator is at rest and in an unloaded condition (e.g., not subject to any external force or pressure). In this unloaded condition, the elongate body may be at or near its maximum diameter. An unexpanded configuration may refer to the elongate body in its collapsed state. In this case, collapse of the elongate body may occur by physical compression or by application of vacuum pressure to the elongate body or the outer membrane to substantially reduce the diameter of the elongate body. The expanded deployed configuration may refer to the state of the elongate body after positioning at the target tissue, which may include a diameter that the elongate body accommodates to, once situated within the confines of tissue anatomy. Since the anatomy can be irregular in diameter and stiffness, the applicator may assume various diameters along its axial length as it conforms to the anatomical contours of the tissue. The elongate body may passively expand from an unexpanded configuration. In other instances, the expanded deployed configuration may be influenced by the volume and/or pressure of the fluid (e.g., air or saline) within a membrane substantially surrounding the elongate body in variations where a membrane is included. It may be in the state of the elongate body after expansion from an unexpanded state or from further expansion of the initial expanded configuration. In some instances, the deployed expanded configuration is the initial expanded configuration. The elongate body may be compliant to enhance conformability of the applicator to one or more tissue surfaces. In some variations, the distal end of the brachytherapy applicators is shaped to help conform the distal end to the tissue surfaces.

In other variations, the elongate body includes a plurality of peripheral lumens. The plurality of peripheral lumens may be spaced within the elongate body in any suitable manner. For example, they may be spaced about the circumference of the elongate body. The peripheral lumens may be symmetrically positioned within the elongate body, asymmetrically spaced within the elongate body, equally spaced apart in the elongate body, unequally spaced within the elongate body, or combinations thereof. The peripheral lumens may also be oriented to run substantially parallel to the long axis of the elongate body, but other suitable configurations are also contemplated. For example, the peripheral lumens may have a curved, splayed, undulating, or other geometric configuration or pattern within the elongate body.

In other variations, the elongate body comprises one or more opposed pairs of peripheral lumens. For example, the elongate body may include one, two, or three or more opposed pairs of peripheral lumens. Here the maximum distance between at least one pair of opposed peripheral lumens may be at least about 70% to at least about 90% of the outer diameter of the elongate body. The positioning of the peripheral lumens within the elongate body may be determined by the configuration that may help optimize the radiation dose and delivery to target tissues. One or more radiation sources may be placed in the central lumen, one or more peripheral lumens, or a combination thereof. In some variations, the applicators may include one or more lumens for passage of an endoscope therethrough for direct visualization of the anatomy prior to, during, or after positioning of the applicator within the body.

In further variations, a membrane, e.g., a polymer membrane, may substantially surround the conformable elongate body. The membrane may be inflated with a gas or a fluid to enhance conformability of the applicator to surrounding tissues and/or positioning of the applicators within the body. Membrane inflation may also provide a physical feature that allows healthy or normal tissue to be spaced away from the radiation sources within the applicators. One or more of the membrane, central lumen, peripheral lumens, and elongate body, or portions thereof, may be radiopaque, or combinations thereof may be radiopaque. It should be understood that "radiopaque," as used herein, refers to the applicator or components thereof, e.g., the membrane, central lumen, peripheral lumens, elongate body, or portions thereof, being visible by an imaging device, e.g., x-ray, computed tomography, or magnetic resonance imaging, but not being so prominent that clinically significant artifact is produced.

In one variation, the applicator is a gynecological brachytherapy applicator comprising a conformable elongate body having a proximal end and a distal end that defines a central lumen at least partially therethrough, and having at least one peripheral lumen at least partially therethrough, where the elongate body has an initial expanded configuration, an unexpanded configuration for advancement of the applicator to a target tissue, and an expanded deployed configuration.

In another variation, the applicator is a gynecological brachytherapy applicator including a substantially cylindrical conformable elongate body having a proximal end and a distal end, the elongate body comprising a foam and defining a central lumen at least partially therethrough and having a plurality of peripheral lumens at least partially therethrough. In this variation, the gynecological brachytherapy applicator also includes a polymer membrane substantially surrounding the conformable elongate body, where the elongate body has an initial expanded configuration, an unexpanded configuration for advancement of the applicator to a target tissue, and an expanded deployed configuration.

In yet another variation, the applicator is a gynecological brachytherapy applicator including a substantially cylindrical conformable elongate body having a proximal end and a distal end that defines a central lumen at least partially therethrough, and further comprising at least one pair of opposed peripheral lumens at least partially therethrough, the at least one pair of opposed peripheral lumens being oriented substantially parallel to the longitudinal axis of the elongate body. In this variation, the maximum distance between the at least one pair of opposed peripheral lumens is at least about 70% of the outer diameter of the elongate body, and the elongate body has an initial expanded configuration, an unexpanded configuration for advancement of the applicator to a target tissue, and an expanded deployed configuration. Here the conformable elongate body is also imageable by computed tomography and magnetic resonance imaging.

Methods for using the brachytherapy applicators for delivering radiation therapy to tissues to treat various proliferative conditions are also described. In general, these methods involve inserting a brachytherapy applicator into a body region, e.g., the vaginal canal, expanding and securing the applicator, confirming its position, dose planning, including calculating (predetermining) a dose cloud shape, and loading a radiation source within the applicator. In one variation, a drug may also be delivered from the applicator in addition to radiation.

In some variations, the methods include advancing a gynecological brachytherapy applicator adjacent to a target tissue, where the gynecological brachytherapy applicator comprises a substantially cylindrical conformable elongate body having a proximal end and a distal end that defines a central lumen at least partially therethrough, and further having at least one pair of opposed peripheral lumens at least partially therethrough. In this variation, the at least one pair of opposed peripheral lumens are oriented substantially parallel to the long axis of the elongate body, and the elongate body has an initial expanded configuration, an unexpanded configuration for advancement of the applicator to a target tissue, and an expanded deployed configuration. Here the conformable elongate body is imageable by computed tomography and the radiation therapy produces a pre-determined dose cloud shape.

Systems for delivering radiation therapy are also described. In general, the systems may include one or more brachytherapy applicators as described herein, one or more removable sheaths, one or more removable handles, or combinations thereof. The systems may provide the applicators, sheaths, and handles as separate components, or may provide the applicators preloaded within the sheaths and/or handles. Pressurized fluid sources for expanding and/or collapsing the elongate body or inflating the membrane may also be included. In some instances, the system may also include one or more radiation sources.

BRIEF DESCRIPTION OF THE DRAWINGS

FIGS. 6A-6C depict one illustrative variation of an inflatable spacer that can be used to space normal or healthy tissues from radiation sources. FIG. 6A provides a top view of the inflatable spacer; FIG. 6B shows a transverse cross-sectional view of the inflatable member (balloon) shown in FIG. 6A; and FIG. 6C shows the inflatable member depicted in FIGS. 6A and 6B conforming to the surface contour of a target tissue.

FIG. 7A shows a side cross-sectional view of the applicator. FIG. 7B shows a transverse cross-sectional view along line A-A of the applicator in FIG. 7A. In FIG. 7C, a layer of adhesive that uniformly spaces the peripheral lumens from the outer surface of the applicator in FIG. 7B is shown.

FIG. 8A is a perspective view of the removable handle; FIG. 8B is a view of the slots at the distal end of the removable handle for engaging one or more peripheral lumens; FIG. 8C is a perspective view of a brachytherapy applicator in its unexpanded (e.g., collapsed) configuration coupled to the removable handle; and FIG. 8D shows the brachytherapy applicator of FIG. 8C in its initial expanded configuration.

DETAILED DESCRIPTION

Figure 1:
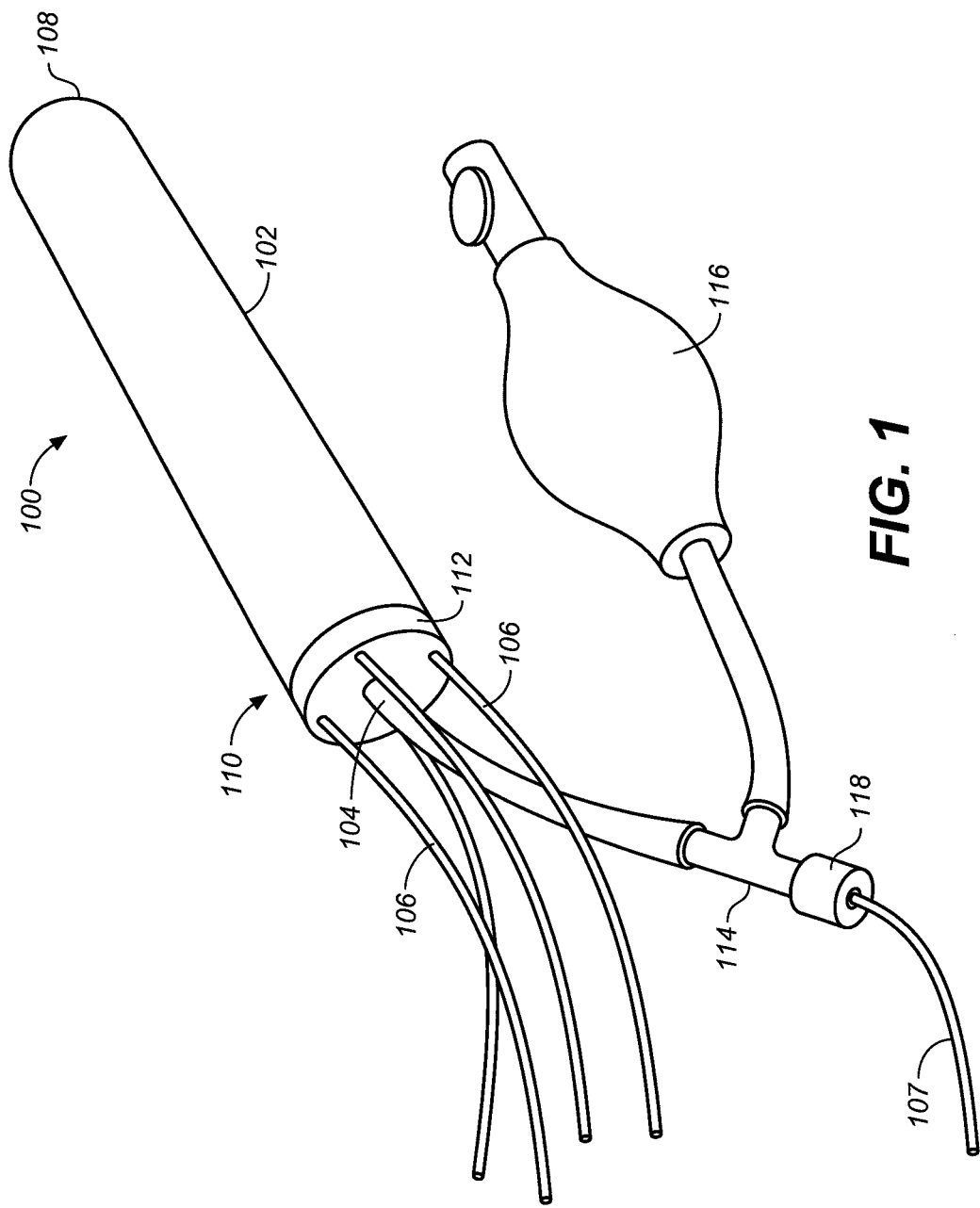
FIG. 1 is a perspective view of one variation of the brachytherapy applicators described herein.

Described here are conformable applicators and systems for use in brachytherapy. With these applicators, custom-shaped dose clouds may be provided to help optimize radiation therapy. For example, the dose clouds may be created via CT-based three-dimensional volumetric dose planning software to create a dose cloud covering the target tissue. Any suitable dose cloud configuration that corresponds with a prescribed dose regimen may be generated, keeping in mind to minimize the amount of radiation delivered to healthy or normal tissues. For example, the dose may be delivered in such a manner that about 85% of the target volume receives about 85% of the therapeutic dose (85-85). Other coverage ranges may be achieved as well, e.g., about 90-90, about 95-90, and about 95-95. Methods for delivering radiation using the applicators to treat various proliferative conditions such as cancers are also described. The applicators may be utilized in any area of the body that may benefit from radiation therapy. In some variations, the applicators are used to treat gynecological cancers, other female cancers, urinary and prostate cancers, and anal/rectal cancers. In other variations, the applicators are used to treat tissues in the abdominal cavity. In still other variations, the applicators are used to access and treat tissues in the head and neck region and tissues not previously mentioned that reside in the retroperitoneal space. The term "tissue" as used herein generally refers to both groups of cells that perform a particular function, and organs, which are aggregates of tissues. In some instances, the applicators may be configured to deliver an active agent, e.g., a chemotherapeutic agent, to body tissues in addition to radiation.

I. Applicators

The brachytherapy applicators described here may have any suitable configuration. Due to their conformability and dose sculpting nature, the brachytherapy applicators may be generally configured to provide a radiation dose profile that helps to maximize the therapeutic dose delivered to a volume of the target tissue while helping to minimize dose to adjacent normal structures. In general, the applicators include an elongate body having a central lumen and at least one peripheral lumen, both of which extend at least partially through the elongate body. The elongate body is generally conformable, e.g., it is both flexible in bending and also compressible in the radial direction. The elongate body may also be compressible in the radial direction so that its diameter may be substantially reduced to facilitate insertion into the body. A membrane may also be included that substantially surrounds the elongate body. The diameter of the applicator may be reduced by compression of the elongate body, e.g., an elongate body made of foam, via a removable sheath or sleeve, or by drawing a vacuum on the membrane or elongate body, thereby compressing the elongate body to a smaller overall diameter. In some variations, the elongate body may be configured to have an initial expanded configuration, an unexpanded configuration, and an expanded deployed configuration. It should be understood that in some instances the initial expanded configuration is the expanded deployed configuration. The brachytherapy applicators may be made from any biocompatible material that does not interfere with the delivery of radiation to target tissues or compromise applicator visualization (e.g., by x-ray, CT, or MRI) during placement and dose planning, and which also does not degrade upon exposure to the radiation source. The brachytherapy applicators may also be made to be disposable between dose fraction delivery, or at the completion of all dose fractions for the patient.

The elongate body may be of any suitable size, shape, or geometry. For example, the elongate body may be substantially cylindrical or radially asymmetric. With respect to length, the elongate body may be between about 3.0 cm to about 20 cm, between about 3.0 cm to about 15 cm, about 3.0 cm to about 12 cm, about 3.0 cm to about 10 cm, about 3.0 cm to about 8.0 cm, or about 3.0 cm to about 5.0 cm in length. The distal end of the elongate body may be shaped to enhance conformability of the applicator to tissue surfaces and to secure positioning of the applicator during the course of brachytherapy, or to enhance dose shaping ability. In one variation, the distal end of the elongate body is rounded. In another variation, the distal end of the elongate body is funnel shaped. In further variations, the distal end of the elongate body is flat. In other variations, the distal end may be relatively blunt, tapered, bulbous, ellipsoid, or spherical.

Any suitable material may be used to make the elongate body, so long as the material has the aforementioned radiation compatibility and resistance properties. In general, the material is porous and compliant, and capable of forming an applicator that conforms to various tissue surfaces. In comparison to rigid applicators, such compliant and conformable applicators may be easier and less traumatic to insert, and more comfortable after positioned in situ. The conformable nature of the applicators may also provide improved conformance between the target tissue surfaces and the radiation source(s), which in turn may improve dose shaping. The material used to make the elongate body may also be imageable (e.g., visible without creating clinically significant artifact). The ability to image the applicator may be useful in the dose planning process.

In one variation, the elongate body is made from foam. The foam may be of the open cell type and have various conformability and/or compressibility characteristics. Exemplary open cell foams include without limitation, polyester foam, polyurethane foam, silicone foam, and thermoplastic elastomer foam. The applicators may also be made with foams having different characteristics. For example, the applicators may be made with foam that is less conformable at the proximal end and more conformable at the distal end. In some applications, a useful characteristic of foam is its ability to be porous and collapsible enough for the applicator to be compressed to a substantially reduced diameter to provide a low profile during introduction into the body and/or advancement to a target tissue, yet at the same time be resilient and strong enough to provide a matrix of support to stabilize the position and spacing of the peripheral lumens that reside within the foam when the applicator is returned to its initial expanded configuration or has an expanded deployed configuration. When a membrane is included on the elongate body, it may also be useful for the foam employed to be collapsible enough to collapse under the force of the membrane collapsing when negative pressure is applied to the applicator volume within the membrane (e.g., via a syringe or squeeze bulb). When it is not required for an applicator to be in its unexpanded (e.g., collapsed) configuration for advancement, the elongate body may be made of a gel or other soft elastomer.

The brachytherapy applicators described here may also be configured so that radiation therapy is delivered according to a predetermined dose cloud shape, making radiation therapy more precise. This may be attributed in part to an elongate body that may include a central lumen extending at least partially therethrough, and one or more peripheral lumens extending at least partially therethrough, and the ability of the elongate body to maintain a relatively preset or predetermined positioning and spacing of the lumens from the outer surface of the applicators. For example, the elongate body may be configured as a support structure that stabilizes the position of the central lumen and the position and spacing of one or more peripheral lumens containing the radiation sources in the applicator after deployment at the target area. In some variations, the distance between the peripheral lumen(s) and the outer surface of the applicators is held constant by a layer of noncompressible material, e.g., a noncompressible polymer material, that surrounds the peripheral lumen(s) or a portion thereof, and which is flush with the outer surface of the elongate body. The lumens may be positioned within the elongate body in any suitable manner that delivers the appropriate radiation dose and dose cloud shape to target tissues. As previously stated, a central lumen may run at least partially through the elongate body. In some variations, the central lumen may extend beyond the distal end of the elongate body to serve as a tandem. The central lumen may also be used as an inflation/deflation lumen for passage of fluid into or from the elongate body to thereby further expand or collapse it, e.g., by further expanding or collapsing an outer membrane, as further described below.

In some variations, the elongate body comprises a plurality of peripheral lumens. The peripheral lumens may be arranged about (around) the circumference of the elongate body or closer to, and around the central lumen, but as previously stated, the lumens may be positioned within the elongate body in any suitable manner that delivers the appropriate radiation dose and dose cloud shape to target tissues. The peripheral lumens may be symmetrically positioned, asymmetrically positioned, equally spaced apart, unequally spaced apart, or any combination thereof within the elongate body. For example, the peripheral lumens may be symmetrically positioned and equally spaced, or symmetrically positioned and unequally spaced. In other instances, the peripheral lumens may be asymmetrically positioned and equally spaced, or asymmetrically positioned and unequally spaced. The peripheral lumens may be spaced from each other a distance of about 1.0 cm to about 5.0 cm. For example, the peripheral lumens may be spaced about 1.0 cm, about 2.0 cm, about 3.0 cm, about 4.0 cm, or about 5.0 cm apart. The peripheral lumens may also be oriented to run substantially parallel to the long axis of the elongate body. In other variations, the elongate body comprises one or more opposed pairs of peripheral lumens. For example, the elongate body may include one, two, or three or more opposed pairs of peripheral lumens. Here the spacing is a maximum distance between at least one pair of opposed peripheral lumens, which may be at least about 70%, at least about 72%, at least about 75%, at least about 80%, at least about 85%, or at least about 90% of the diameter of the elongate body in its initial expanded configuration or expanded deployed configuration. The diameter of the elongate body in the unexpanded configuration may range from about 1.0 cm to about 3.0 cm. In its initial expanded configuration, the diameter of the elongate body may range from about 2.0 cm to about 5.0 cm.

The radiation source(s) may also be included in the lumens in any suitable manner that delivers the appropriate radiation dose and dose cloud shape to the target tissues. In one variation, the peripheral lumen(s) contains the radiation source(s) within the elongate body. In another variation, the central lumen contains the radiation source. In some instances, a combination of the central lumen and one or more peripheral lumens contain radiation sources. The central lumen and peripheral lumens may be formed from a flexible polymeric material, e.g., from fluoropolymers, polyetheretherketone (PEEK), polyethylene, polyethylene terephthalate, silicone, polyamides, Pebax® polyether block amide, and the like.

A membrane that substantially surrounds the elongate body may also be provided on the applicators. As further described below, the membrane may help to securely position the applicator in situ during the entire course of brachytherapy. The membrane may be a flexible film that can be variously secured to the elongate body. In one variation, the membrane is secured to the proximal and distal ends of the elongate body. In another variation, the membrane is attached or secured to the elongate body at one or more intervals along its length. Adhesives such as silicone adhesives and other polymer adhesive well known in the art, or an external elastomer ring may be used to secure the membrane to the elongate body. The membrane may be made from any suitable material that provides the physical strength and elasticity required when using the applicators. Exemplary materials include fluoropolymers, natural and synthetic latex, polyurethane, silicone, thermoplastic elastomers, and the like.

In some variations, the elongate body may be configured with a proximal port and a plurality of body ports along the length of the central lumen. The proximal port may be adapted to connect with a source of pressurized fluid, e.g., a syringe, bulb, tank or reservoir with a pump, etc. The pressurized fluid may be any biocompatible gas such as air or a biocompatible liquid such as normal saline that is capable of expanding the elongate body when flowing from the pressurized fluid source through the central lumen and body ports into the elongate body. Prior to insertion and advancement of the applicator, the proximal port may be configured to connect with a vacuum source that withdraws air from the elongate body in its initial expanded configuration to provide an unexpanded (e.g., collapsed) configuration. After advancing the applicator to its appropriate position near or adjacent to the target tissue, the vacuum pressure may be released, thereby allowing the elongate body to expand to its expanded deployed configuration. The vacuum may also be used to aspirate previously delivered pressurized fluid within the elongate body when removal of the applicator is desired. In other variations, an unpressurized fluid may be used to expand the elongate body.

In still other variations, the fluid may be further used to inflate the membrane that may substantially surround the elongate body. Membrane inflation may help secure the position of the applicator within the body and/or enhance conformability of the elongate body to the contour of tissue surfaces. Furthermore, membrane inflation may also create a fluid-filled area between the elongate body and membrane surface that may space healthy or normal tissues away from tissues targeted for radiation treatment.

Referring to the figures, an exemplary brachytherapy applicator is illustrated in FIG. 1. In this variation, brachytherapy applicator (100) includes an elongate body (102), a central lumen (104), and a plurality of peripheral lumens (106). Here the distal end (108) of the brachytherapy applicator (100) is rounded in shape, but other shapes may be used. For example, depending on such factors as the space or cavity of insertion, contour of the tissue surface to be treated, presence of an intact cervix, and amount of spacing desired from healthy or normal tissues, the distal end (108) may be modified to form a funnel or other concave shape, a taper, a point (see FIG. 2), a flattened surface (FIG. 7A), an ellipsoid or spherical shape, or any other useful shape. The rounded shape of distal end (108) and the may be useful for delivery of radiation to vaginal cuff tissues after hysterectomy. Here the elongate body is shown as being cylindrical, but it can also have any other suitable shape, e.g., it can be ellipsoid or spherical. The shape of the elongate body may depend on the geometry of the tissue area that the applicator is placed. The peripheral lumens (106) may also run substantially parallel to the long axis of the elongate body, but in some instances the peripheral lumens may bend or curve to follow the shape of the elongate body and/or tissue to be treated. For example, in FIG. 5 the peripheral lumens follow the contour of the elongate body and then curve at the distal end to help conform the distal end to the anatomical contour of the tissue to be treated (in this case the cervix). At the proximal end (110) of elongate body (102), a hub (112) is provided with a plurality of openings for passage therethrough of central lumen (104) and peripheral lumens (106). Hub (112) may be made from silicone or any other functionally appropriate material, and have a diameter that may be less than or equal to the diameter of the applicator in its initial expanded configuration.

Also shown in FIG. 1 is a T-connector (114) for connecting a pressurized fluid source (116) to the central lumen (104). Pressurized fluid source (116) is shown in FIG. 1 as a bulb, but other pressurized fluid sources, e.g., syringes and pumps, may also be employed. Pressurized fluid source (116) may further be equipped with a valve (not shown) that prevents backflow of fluid from the central lumen (104) when the pressure source (116) is detached. In some instances, an additional lumen (107) may be placed coaxially within central lumen (104), e.g., to deliver the radiation source or a removable stiffening stylet (not shown). In these instances, a seal (118) or hub may reside around the additional lumen (107) or stylet and may be joined to T-connector (114). The seal (118) or hub may provide a friction fit with additional lumen (107) or the stylet to maintain the position of additional lumen (107) or stylet within central lumen (104).

Figure 7A:
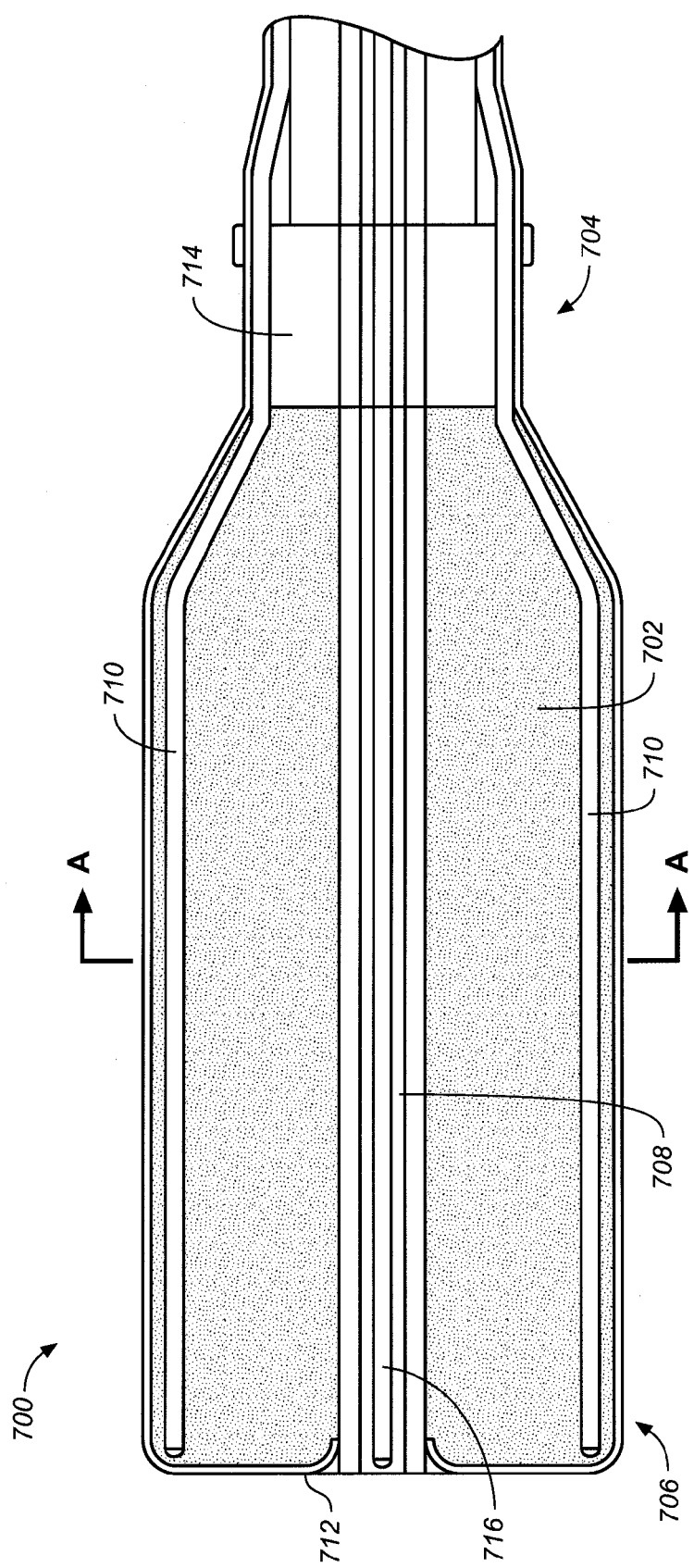
FIGS. 7A-7C depict another exemplary brachytherapy applicator.
Figure 7B:
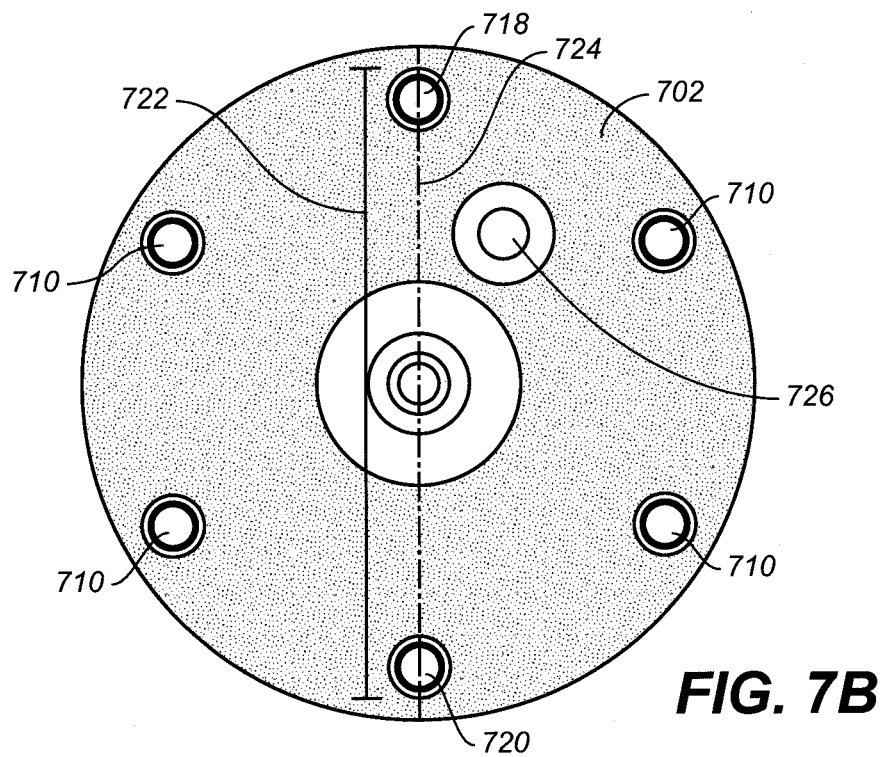

Another exemplary brachytherapy applicator is shown in FIGS. 7A-7B. In FIG. 7A, brachytherapy applicator (700) includes an elongate body (702) having a proximal end (704) a distal end (706), a central lumen (708), and a plurality of peripheral lumens (710). The peripheral lumens (710) in this variation run substantially parallel to the longitudinal axis of elongate body (702). Although the distal end (706) is shown as a flattened surface (712), the distal end may be of any suitable shape. The flattened distal end (712) may be useful for delivery of radiation to vaginal cuff tissues after hysterectomy. The central lumen (708) and peripheral lumens (710) run through a hub (714) at the proximal end (704). In this variation, an additional lumen (716) for slidable advancement of a radiation source within central lumen (708) is also shown. Here the brachytherapy applicator also includes six peripheral lumens (710), as illustrated in FIG. 7B, which is a transverse cross-sectional view taken along line A-A of the applicator shown in FIG. 7A. It is understood that the number of peripheral lumens depicted here is non-limiting, and that any suitable number, positioning, and spacing of peripheral lumens may be incorporated into the applicators.

Referring to FIG. 7B, the plurality of peripheral lumens (710) are symmetrically positioned and equally spaced about the circumference of elongate body (702). However, they could be symmetrically positioned and unequally spaced, asymmetrically positioned and equally spaced, or asymmetrically positioned and unequally spaced within the elongate body. In this variation, the peripheral lumens (710) are equally spaced from each other a distance of about 2.0 cm. Also in this variation, the peripheral lumens form opposed pairs within the elongate body. Peripheral lumens that form an opposed pair are about 180° from each other when measured about the circumference of the elongate body. Here for example, peripheral lumens (718) and (720) form an opposed pair given that they are spaced 180° from each other about the elongate body circumference. In this variation, the opposed pair of peripheral lumens (718) and (720) are spaced by a maximum distance (722) that is at least about 70% of the outer diameter (724) of the elongate body. The maximum distance (722) between peripheral lumens is generally measured from the luminal surfaces closest to the outer surface of the elongate body. In some variations, the distal end of the elongate body includes an opening (not shown) that communicates with the central lumen for slidable advancement of an additional lumen, a tandem, etc., therethrough. An inflation lumen (726) separate from the central lumen (708) may also be included.

Figure 7C:
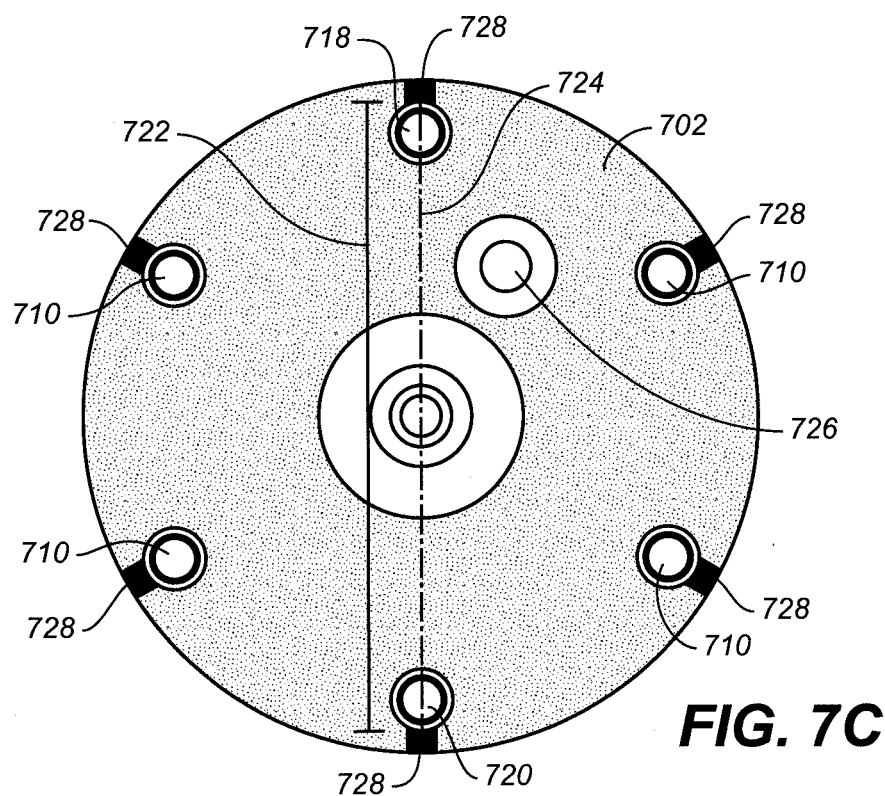

As previously stated, radiation therapy may be delivered in precise pre-determined dose cloud shapes by stabilizing the spacing of the one or more peripheral lumens from the outer surface of the elongate body. Referring to FIG. 7C, a layer of noncompressible material (728) is shown surrounding a portion of peripheral lumens (710). The layer (728) helps to keep peripheral lumens (710) a pre-determined distance from the elongate body outer surface to, e.g., reduce dosimetric hot spots to the immediately adjacent tissue (e.g., vaginal wall mucosa). The distance between the peripheral lumens and elongate body outer surface may be about 2.0 mm, about 3.0 mm, about 4.0 mm, or about 5.0 mm. The noncompressible material may be a material of any suitable durometer or hardness that maintains the pre-determined distance between the peripheral lumens and the elongate body outer surface, and yet still provides for conformability and flexibility of the adjacent lumens and elongate body. For example, materials such as polymers may be used. Exemplary polymers include without limitation, fluoropolymers, natural and synthetic latex, polyurethane, silicone, other thermoplastic elastomers, and the like. In one variation where the elongate body is made from foam, silicone, e.g., a silicone adhesive, may be used to provide this layer, whereby the silicone material can penetrate the nearby cells of foam to effectively bond the foam to itself after the peripheral lumen has been placed into the foam elongate body during fabrication of the applicator. The layer including the noncompressible material, or portions thereof, may also be made to be radiopaque. The radiopacity should allow visualization of the noncompressible material by, e.g., computed tomography or magnetic resonance imaging, but not be so prominent so that clinically significant artifact is produced.

Figure 2:
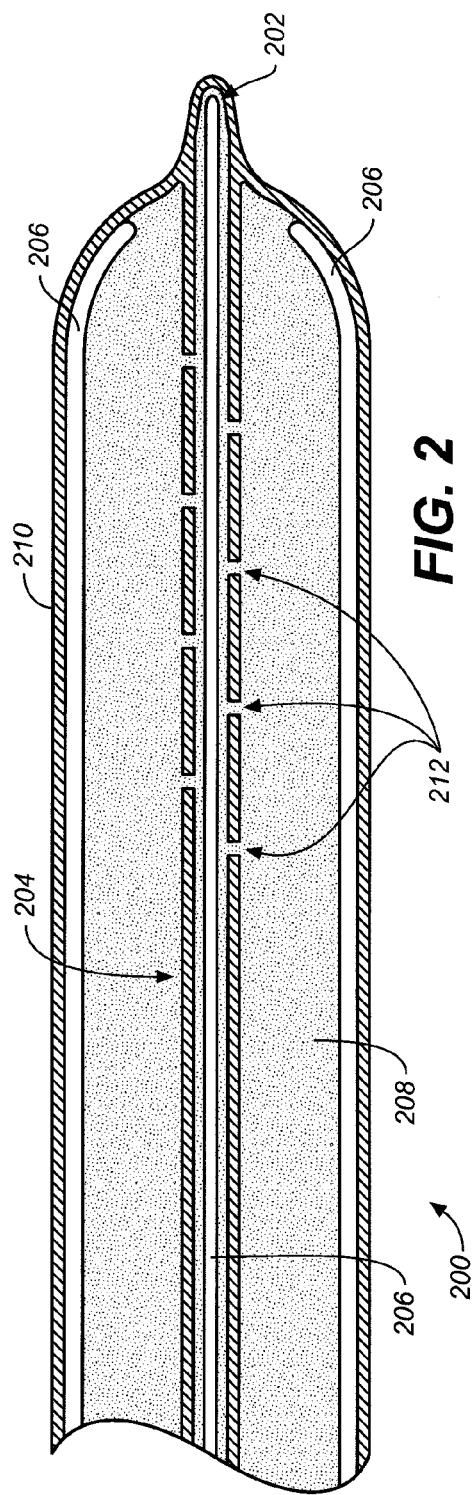
FIG. 2 depicts a longitudinal cross-section of an illustrative brachytherapy applicator.

In the variation depicted in FIG. 2, brachytherapy applicator (200) is configured at the distal end with peripheral lumens (206) that may conform to the distal end of the applicator, including applicator tip (202). The longitudinal cross-section shows how central lumen (204) and peripheral lumens (206) extend through the elongate body (208). On the surface of the elongate body (208) is a membrane (210), which may be a flexible film. A plurality of body ports (212) may also be included along the central lumen (204). The flow of fluid through the central lumen (204) and body ports (212) into the material of elongate body (208) expands the elongate body (208). Due to the porous nature of the elongate body material, inflation of the elongate body (208) may also result in a space between the membrane (210) and the elongate body (208) (see FIG. 5). By varying the distensibility in certain areas of the membrane and/or varying points of membrane securement to the elongate body, inflation of the membrane may provide many different applicator configurations. Withdrawal of fluid from the material of elongate body (209) may also occur through body ports (212) and central lumen (204) to collapse the elongate body (208). Alternatively, the fluid may flow through a separate port (not shown) in the hub instead of through the central lumen to expand or collapse the elongate body.

Figure 3:
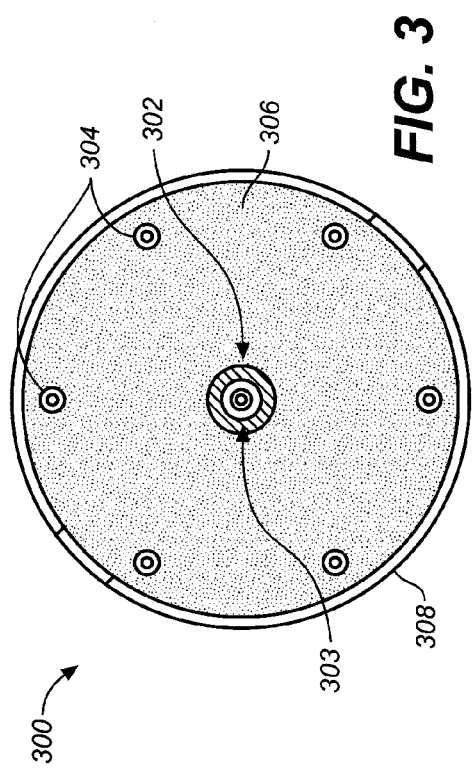
FIG. 3 provides a transverse cross-sectional view of a brachytherapy applicator according to another variation.

In the transverse cross-section provided in FIG. 3, brachytherapy applicator (300) is provided with a central lumen (302) and a coaxially positioned additional lumen (303). Peripheral lumens (304) are also supported within the material of the elongate body (306) about 2.0 mm to about 5.0 mm from membrane (308), which surrounds elongate body (306). Although the peripheral lumens (304) are shown as being positioned around the periphery of the elongate body (306), it should be understood that this is not limiting and other configurations may be employed.

It should also be appreciated that positioning of the applicator may help to facilitate delivery of the radiation dose to the target tissue. Positioning of the brachytherapy applicators described here may be facilitated by employing an elongate body, which in its expanded deployed configuration generally conforms to one or more tissue surfaces. Inflation of the membrane surrounding the elongate body may further enhance in situ fixation of the applicator with a reduced need for traditional gauze packing. Positioning of the brachytherapy applicator may also be achieved by incorporating a radiopaque material such as barium sulfate, bismuth subcarbonate, tantalum, or tungsten into the elongate body, membrane, central lumen, peripheral lumen(s), portions thereof, and/or combinations thereof. Alternatively, one or more radiopaque markers may be used. For example, radiopaque coils, as further described below, may be placed around one more lumens to help with visualization, e.g., by imaging, of the applicator. Exemplary imaging devices include without limitation x-ray, computed tomography, and magnetic resonance imaging devices. Here again it should be understood that the radiopacity should allow visualization by the aforementioned imaging devices, but not be so prominent that clinically significant artifact is produced. In some variations, the brachytherapy applicators substantially lack metal elements to enhance their compatibility with computed tomography and magnetic resonance imaging. In other variations, an endoscope may be used with the applicators to directly visualize the anatomy before, during, or after placement of the applicator within the body. Positioning of the applicator may also be facilitated by using a removable handle, as further described below and shown in FIG. 8, which may be used to push the applicator distally and adjust the rotational orientation of the applicator for initial positioning or repositioning prior to dose delivery.

Another feature of the brachytherapy applicators described here is their ability to push healthy or normal tissues away from the radiation sources by inflation of the membrane. Spacing healthy or normal tissues from the radiation sources may reduce the dose of radiation delivered to them, which in turn helps to reduce the complications associated with brachytherapy. In one variation, an additional inflatable member, e.g., a flat or sheet-like balloon, may be used in combination with the brachytherapy applicators to space normal tissues away from the radiation. When used, the inflatable member may be configured to inflate during radiation dose delivery to create extra distance between the radiation source and normal tissues, and to deflate between delivery of radiation fractions. For example, the inflatable member may be placed at the time of hysterectomy between the rectum and vaginal wall and/or the bladder and the vaginal wall, inflated during dose delivery, and then deflated between dose fractions, and then removed after the final dose fraction.

The radiation sources that may be used with the brachytherapy applicators include without limitation, radioactive liquids, radioactive gels, and radiation seeds. By "radiation seeds" it is generally meant solid or substantially solid radioactive particles, pellets, capsules, rods, needles, wires, and the like. The radiation source may include radionuclides such as cesium, iridium, iodine, cobalt, palladium, strontium, yttrium, gold, ruthenium, californium, and combinations thereof.

In some variations, the brachytherapy applicators are also configured to deliver a drug. It should be understood that the terms "agent" and "drug" are used interchangeably herein throughout. The brachytherapy applicators may deliver any suitable drug to the target tissue, areas adjacent thereto, and/or the general area of applicator placement. For example, drugs that reduce tissue swelling, protect against free radical damage, provide anesthesia, or reduce pain may be delivered. Chemotherapeutic/antiproliferative agents may also be delivered.

Examples of chemotherapeutic/antiproliferative agents that may be delivered using the brachytherapy applicators described here include, but are not limited to, alkylating agents or other agents which directly kill cancer cells by attacking their DNA (e.g., cyclophosphamide, isophosphamide); nitrosoureas or other agents which kill cancer cells by inhibiting changes necessary for cellular DNA repair (e.g., carmustine (BCNU) and lomustine (CCNU)); antimetabolites or other agents that block cancer cell growth by interfering with certain cell functions, usually DNA synthesis (e.g., 6-mercaptopurine and 5-fluorouracil (5FU); compounds that act by binding or intercalating DNA and preventing RNA synthesis (e.g., doxorubicin, daunorubicin, epirubicin, idarubicin, mitomycin-C and bleomycin); plant (vinca) alkaloids and other agents derived from plants (e.g., vincristine and vinblastine); steroid hormones; hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, steroidal inhibitors such as exemestane); antiangiogenic proteins, small molecules, gene therapies and/or other agents that inhibit angiogenesis or vascularization of cancers (e.g., meth-1, meth-2, thalidomide); interferons; interleukins; and combinations thereof.

II. Systems

Figure 4:
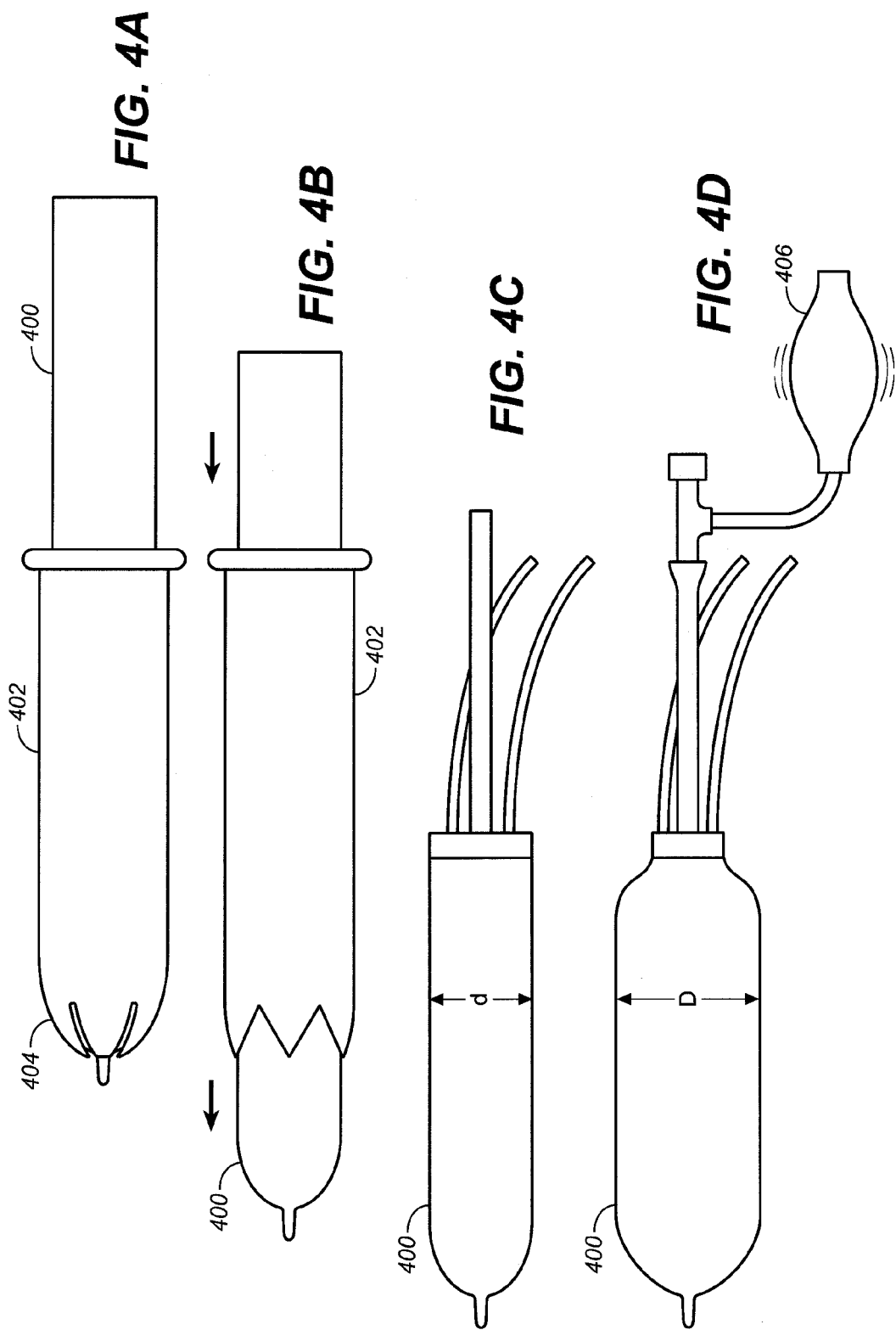
FIGS. 4A-4D demonstrates one variation of how the brachytherapy applicator may be deployed from a sheath and expanded.

In some variations, the systems may include one or more brachytherapy applicators described herein, one or more removable sheaths for housing the applicators during advancement to the target tissue, one or more removable handles for advancement and positioning of the applicators, or combinations thereof. The sheath may be of any suitable design so long as it is are capable of housing and supporting, and in some instances compressing the brachytherapy applicator during insertion into the body and configured for slidable advancement of the applicator therethrough or retraction from the applicator. For example, as shown in FIG. 4, sheath (402) may be a tubular structure having a rounded, multi-leaf tip (404). In one variation, the system may provide the brachytherapy applicator preloaded within the sheath.

In other variations, the systems include one or more removable handles for advancement and positioning of the applicators. The removable handles may range from about 10 cm to about 20 cm in length. For example, they may be about 11 cm, about 12 cm, about 13 cm, about 14 cm, about 15 cm, about 16 cm, about 17 cm, about 18 cm, or about 19 cm in length. The diameter of the removable handles may also vary, and range from about 1.5 cm to about 3.0 cm. In some variations, the diameter of the handle matches the diameter of the applicator in its unexpanded (e.g., collapsed) configuration. The removable handle may include one or more surface features, e.g., a collar, texturing, etc., that helps to prevent slippage of the handle from the hand of the user. A mechanism for repositioning the applicators after initial deployment may also be included. In some variations, as shown in FIGS. 8A-8D, removable handle (800) includes a proximal end (802), a distal end (804), and a body (806). A collar (808) is provided on the proximal end (808), which may help prevent slippage of a user's hand off the handle during advancement of the applicator or repositioning thereof, e.g., due to the presence of lubricant on the handle. The collar (808) may also serve as a stop for the proximal end of a sheath when a sheath is employed. The distal end (804) comprises an opening (810) having a plurality of slots (812) about its circumference. Although six slots are shown in the figure, any suitable number of slots may be included. It should also be understood that the slots may be of any suitable size and geometry.

Figure 8A:
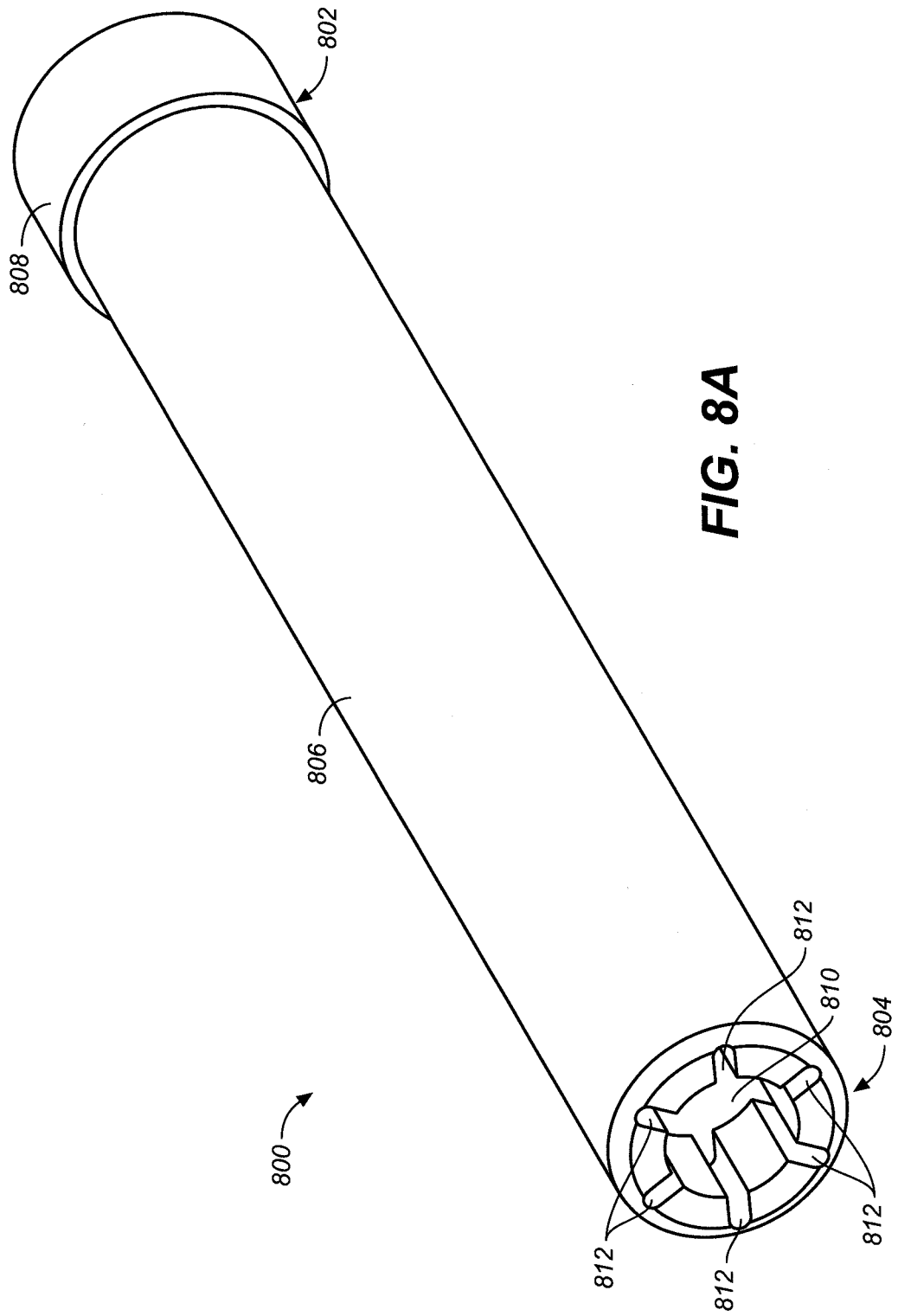
FIGS. 8A-8D depict an exemplary removable handle for positioning brachytherapy applicators at a target tissue. Specifically.
Figure 8B:
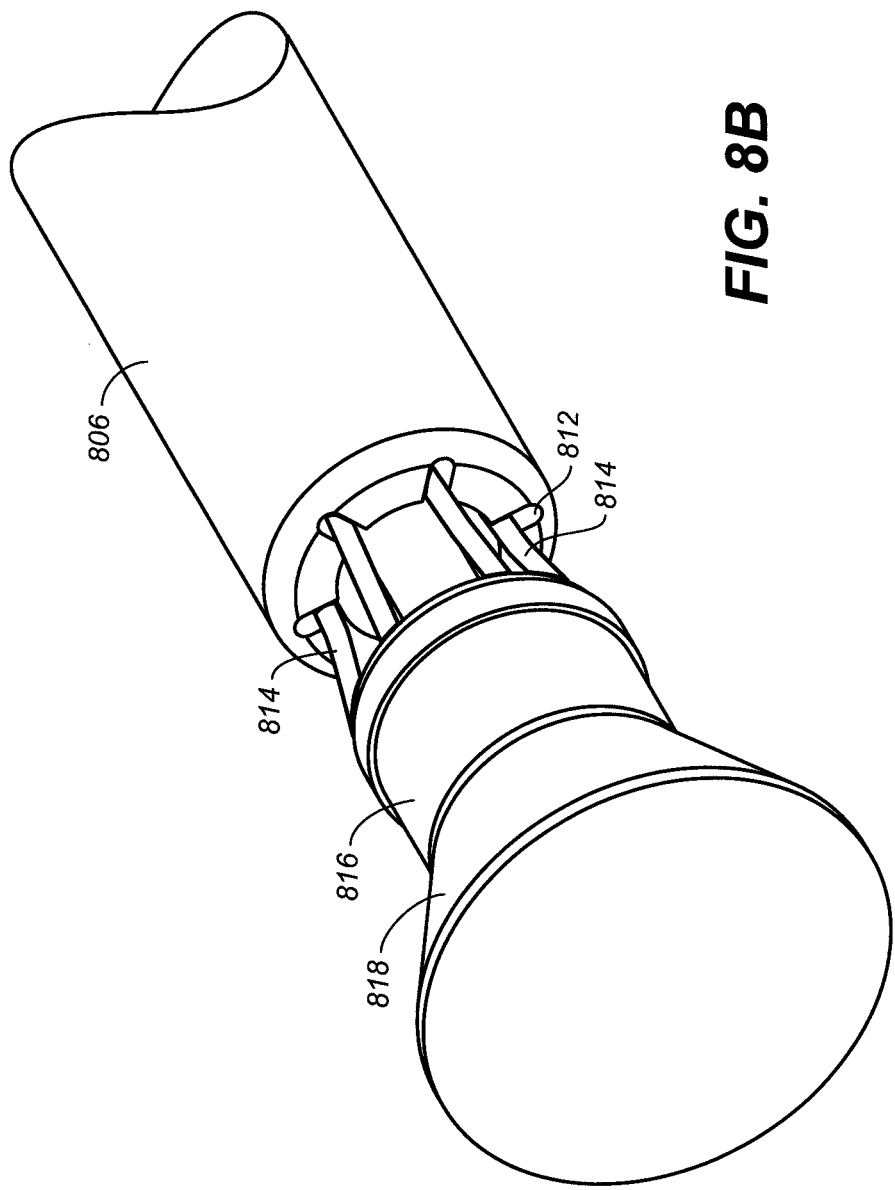
Figure 8C:
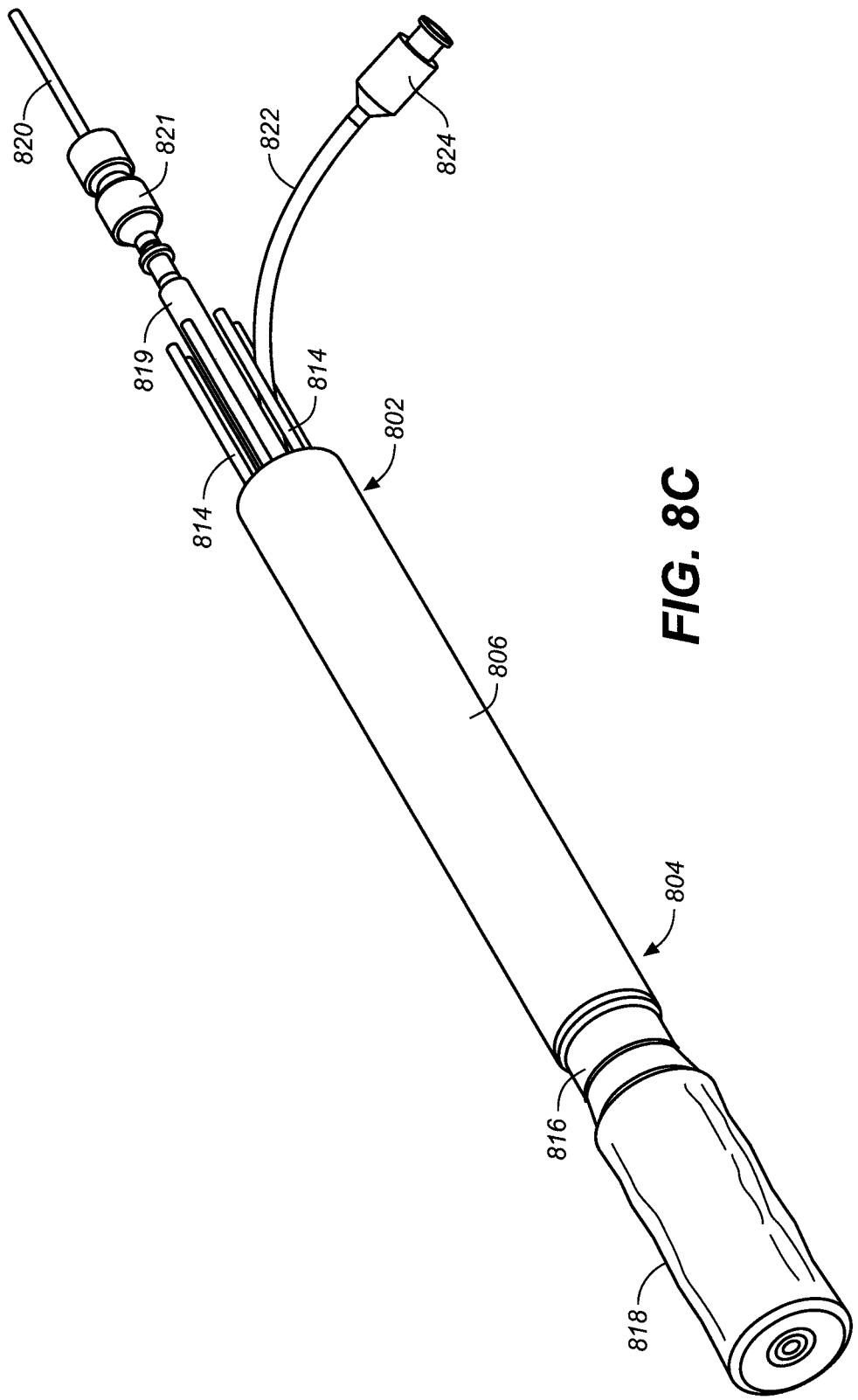
Figure 8D:
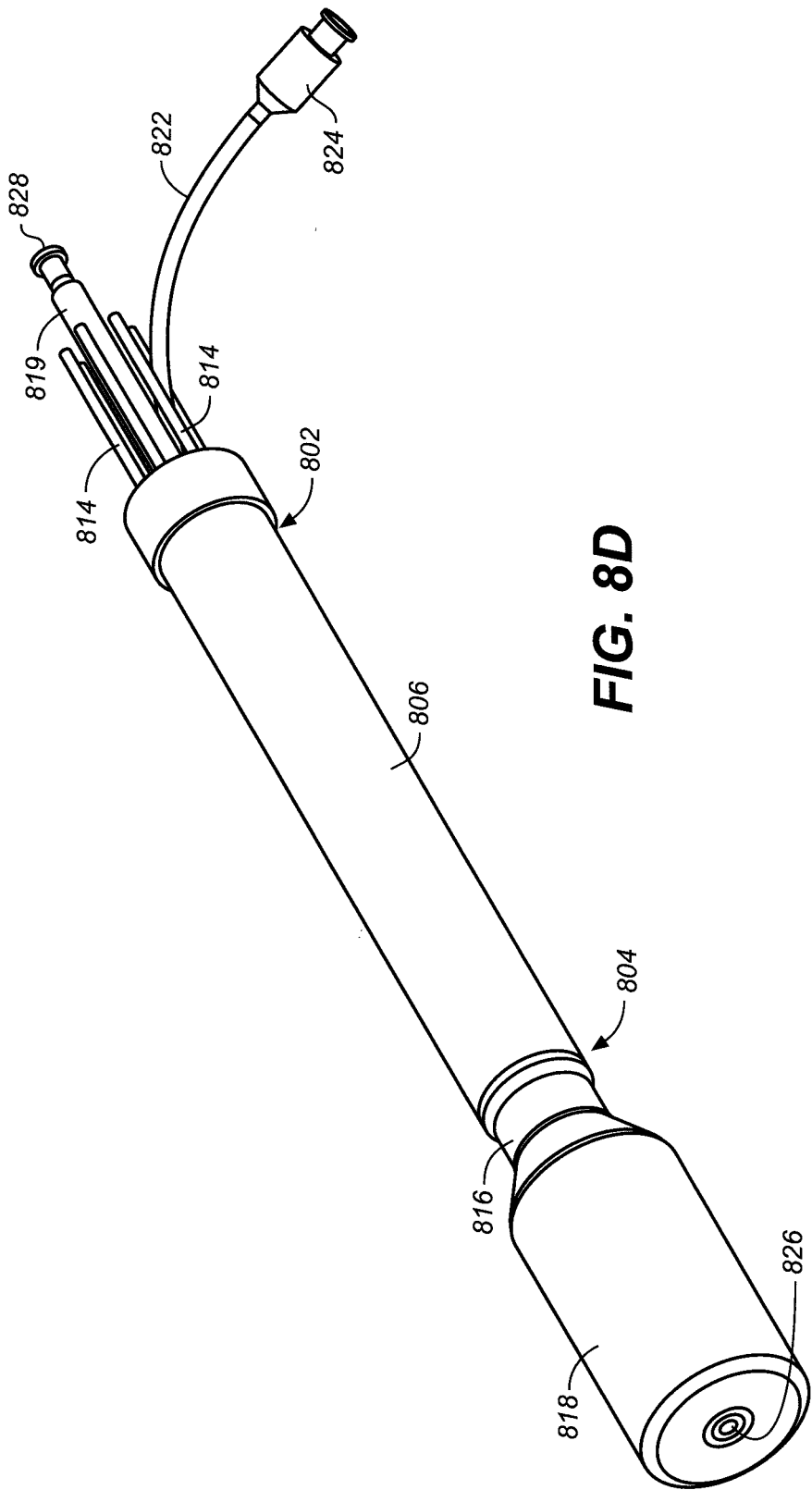
Figure 8E:
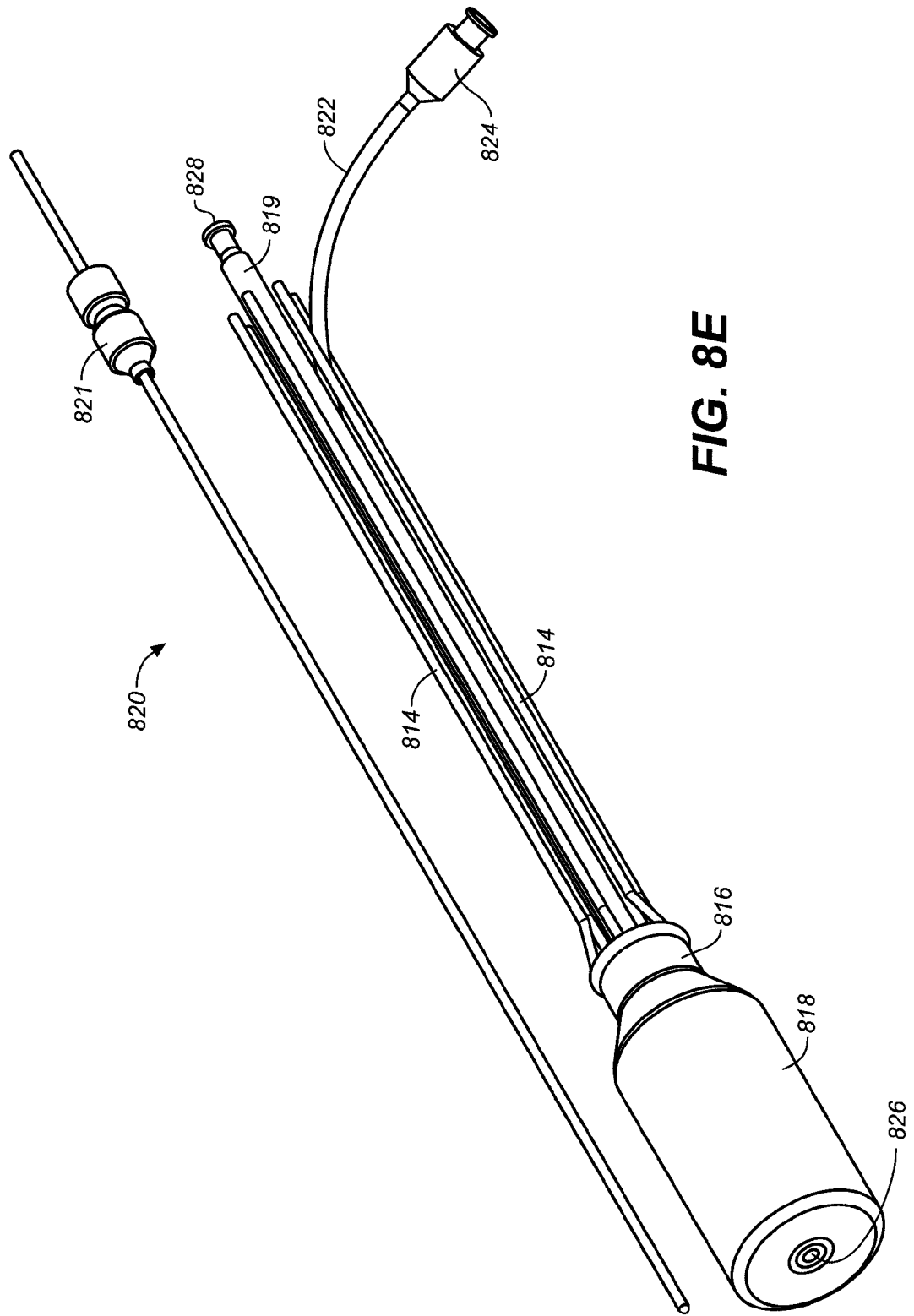
FIG. 8E further depicts an exemplary additional lumen or tandem that may be used with the brachytherapy applicator shown in FIG. 8D.

Referring to FIG. 8B, elongate body (818) of the applicator may be coupled to removable handle (800) by sliding peripheral lumens (814) through opening (810) and placing, e.g., by threading, peripheral lumens (814) into slots (812). The elongate body (818) may then be pushed proximally so that hub (816) approximates opening (810) and slots (812). The applicator may be uncoupled from the removable handle by pulling the removable handle proximally. Removable handle may also be recoupled to the applicator by again sliding the peripheral lumens through the opening in the distal end of the handle. Placement of the peripheral lumens within the slots creates a mechanism by which torque can be applied to the applicator to reposition it in relation to the target tissue. In some variations, the applicator includes a braided or otherwise reinforced central lumen (not shown) that helps to transmit a torque to the applicator. FIG. 8C shows an applicator having an elongate body (818) in its unexpanded (e.g., collapsed) configuration coupled to the removable handle. FIG. 8D shows an applicator having an elongate body (818) in its expanded configuration coupled to the removable handle. An inflation source as previously described may be removably attached to inflation lumen (822) via connector (824) for expanding elongate body (818) from its unexpanded (e.g., collapsed) configuration to its expanded (or expanded deployed) configuration. Also shown is an opening (826) at the distal end of elongate body (818) in communication with central lumen (819). Here this allows an additional catheter (820), e.g., an additional source catheter or tandem, to be inserted into the proximal hub (828) of central lumen (819) and advanced such that the distal end of the additional catheter (820) resides at or near the distal end of the elongate body. Varying the position of the hub (821) of additional catheter (820) with respect to the central lumen proximal hub (828) can vary the position of the distal tip of the additional catheter (820). In some variations, e.g., when positioning of the additional lumen into the cervix or other adjacent target tissue may be useful, a longer variation of additional catheter (820) may be advanced through opening (826) in the distal end of elongate body (818) so that it extends out the distal end to act, e.g., as a tandem. Additional catheter (820) is shown uncoupled to the applicator in FIG. 8E.

The systems may also include a plurality of brachytherapy applicators (with or without a sheath) that vary in length, shape at the distal end, number of peripheral lumens, initial expanded diameter, unexpanded (e.g., collapsed) diameter, expanded deployed diameter, or combinations thereof. The systems may also include one or more additional lumens for slidable receipt within the central lumen. In other variations, the systems may include one or more applicators and one or more radiation sources.

The systems may also be provided with instructions for using the brachytherapy applicators. Specifically, the instructions may provide information on how to collapse the applicator, place the sheath around the applicator, insert and/or remove the applicator to or from the body, or load the radiation source into the lumens of the applicator. The radiation source may be a radioactive liquid or a radiation seed. The radiation seed may be of the low dose variety (e.g., Iodine or Palladium) or the seed may be of the high dose rate variety typically delivered via remote afterloaders (e.g., Iridium). The radiation source may also be of the miniature x-ray tube variety as offered by Xoft, Inc. In this instance, the applicator lumens might be larger in diameter than those used for remote afterloader-delivered radionuclide seeds (e.g., 3.0 mm to 4.0 mm diameter lumens for mini x-ray tube sources versus 1.0 mm to 2.0 mm diameter lumens for seed sources).

III. Methods of Use

The brachytherapy applicators described here may be used in any area of the body that may benefit from radiation therapy. As previously mentioned, the brachytherapy applicators may be used in, e.g., natural or surgically created cavities or spaces within the pelvis, abdomen, or head and neck region. With respect to the pelvis, intravaginal, cervical, and intrauterine applications may be useful. The brachytherapy applicators may also be used in the thoracic cavity, pleural space, or retroperitoneal space.

The brachytherapy applicators can also be used to deliver radiation that is useful in treating any body tissue affected by a proliferative condition. Proliferative conditions include tumors, cancers, or other manifestations of abnormal cellular division. For example, the brachytherapy applicators may be used to treat adenocarcinomas, carcinomas, leukemias, lymphomas, myelomas, sarcomas, and mixed-type cancers. Gynecologic cancers such as cervical cancer, endometrial cancer, uterine cancer, ovarian cancer, and vaginal cancer may benefit from treatment with the brachytherapy applicators described herein due their conformable and spacing features. Radiation of the vaginal cuff (e.g., after hysterectomy) for endometrial cancer with or without adjuvant pelvic external beam radiation, may also be performed with the applicators described herein. Radiation therapy for proliferative conditions is generally administered over a period of time in partial doses, or fractions, the sum of which comprises a total prescribed dose. For example, about two to about four fractions may be used for vaginal cuff brachytherapy with a total dose of about 10 Gy to about 30 Gy to the target tissue. For cervical cancer, about two to about five fractions may be used with a total dose of about 30 Gy to about 45 Gy to the target tissue. This fractional application takes advantage of cell recovery differences between normal and proliferative tissue, e.g., cancerous tissue, because normal tissue tends to recover between fractions while proliferative tissue tends not to recover or recover at a slower rate.

Treatment planning (dose planning) may occur prior to the initiation of radiation therapy to determine a prescribed dose to be delivered to a volume of the target tissue. In some instances, the prescribed dose may specify a minimum dose to be delivered to a preferred depth outside the treatment cavity (the prescription depth). Other two-dimensional dose prescription regimes may be used as well, e.g., when delivering radiation therapy to the pelvic area. The dose planning process may assess distances from cavity surfaces to skin surfaces or to other radiation sensitive structures (e.g., rectum, bladder, small bowel) and may use these distances in combination with the prescribed prescription depth to determine a dose profile and a dose cloud shape. In this manner, the radiation therapy that is delivered to the target tissue in a subject in need thereof may be configured to provide a pre-determined dose cloud shape. The dose cloud may be of any suitable shape. For example, the dose cloud shape may be symmetric with respect to the central axis of the applicator or asymmetric with respect to the central axis of the applicator. The bending flexibility of the applicators described herein, with its highly compressible and conformable surface, combined with its array of spaced peripheral lumens provides for significant patient comfort and dose planning flexibility. Because of the absence of shielding or any metal components in the applicator, three dimensional volumetric-based dose planning with conventional dose planning software (e.g., supplied by Varian or Nucleotron) may be readily accomplished with these applicators. This approach includes three-dimensional imaging of the cavity or body region of interest, e.g., by computed tomography (CT), magnetic resonance imaging (MRI), or x-ray, and may be automated. With these three-dimensional dose planning systems, dose planning may be performed more precisely and more accurately, and with a greater characterization of the dose that is being delivered to the target tissue as well as adjacent normal tissue structures. This type of three-dimensional dose planning may also automate the dose delivery, thereby improving dosing accuracy and safety.

The brachytherapy applicators may be inserted and advanced in any suitable manner. In some variations, the brachytherapy applicators are collapsed outside the body from an initial expanded configuration to an unexpanded configuration. The applicator in its unexpanded configuration is then inserted, e.g., within a body cavity, and advanced to the target tissue. After appropriate positioning, the applicator may then be expanded into its expanded deployed configuration. A sheath may be employed when inserting the brachytherapy applicators, but need not be. When a sheath is used, the brachytherapy applicators may be preloaded in the sheath. Robotic insertion of the applicators described herein is also contemplated.

Given that the brachytherapy applicators are compliant and lack rigid components, they are generally less traumatic to position and secure in the patient. Taking this into consideration, it is contemplated that reduced anesthesia and/or sedation will be needed for applicator placement. In some variations, removable or permanent internal stiffener elements may be employed to facilitate applicator placement. The stiffeners may reside in one or more lumens or may be located elsewhere within the elongate body. In other variations, a hygroscopic laminaria or other gradual cervical dilating device to dilate the cervix prior to inserting a tandem and/or other components of the applicator may be used to facilitate proper applicator placement with reduced anesthesia and/or sedation requirements.

The radiation sources may then be placed within the brachytherapy applicators by any suitable method. For example, the radiation sources may be afterloaded, either by hand (manual afterloading) or by a machine (automatic remote afterloading) after the brachytherapy applicators are positioned. In other variations, hot loading may be employed. With hot loading, the brachytherapy applicator contains the radiation sources at the time of placement into the subject in need of radiation therapy. The radiation therapy that is subsequently delivered by the radiation sources may provide radiation therapy in a pre-determined dose cloud shape, as previously stated.

An exemplary method for inserting the brachytherapy applicators is shown in FIGS. 4A-4D. In FIG. 4A, brachytherapy applicator (400) prior to insertion may be disposed within a sheath (402). As previously mentioned, the brachytherapy applicator and sheath may be provided separately, and the brachytherapy applicator loaded within the sheath prior to insertion, or provided as a preloaded applicator. As shown in FIG. 4B, brachytherapy applicator (400) is inserted by advancing it toward the body, in the direction of the arrows. The depth to which the brachytherapy applicators are inserted into the body may vary according to the body region of insertion, type of cancer being treated, etc. Insertion to the target location in the body may be assisted by direct visualization using an endoscope that may be, e.g., advanced through a lumen of the applicator, or by using an imaging procedure. Exemplary imaging procedures include without limitation, x-ray, CT, and MRI. The sheath (402) is retracted away from the body after reaching its target location. The brachytherapy applicator (400) at this stage is in its initial expanded configuration (see FIG. 4C) and may or may not be completely secured in position. Passive expansion to its initial expanded configuration may securely position the applicator within the body. In other instances, positioning of the brachytherapy applicator (400) may be helped by inflation to its expanded deployed configuration by pressurized fluid source (406), as depicted in FIG. 4D. The compressible and compliant features of the elongate body, which may be made from foam, generally provides a passively conformable applicator capable of conforming to the varied anatomy of patients. Additional inflation of the applicator may create a space between the membrane and the elongate body that increases the distance between the radiation source and adjacent normal tissues to reduce the radiation dose to the normal tissues. Inflation to varying degrees may also modulate securement of the applicator in the desired position by providing increased traction against the walls of the body region in which it is placed. Additionally, the conformable and generally lightweight nature of the brachytherapy applicators described here may reduce the need to use the external fixation devices typically employed to secure the position of conventional gynecological brachytherapy applicators.

Referring now to FIGS. 4C and 4D, brachytherapy applicator (400) has an expanded deployed nominal diameter (D), as shown in FIG. 4D, and an initial expanded nominal diameter (d), as shown in FIG. 4C. When a vacuum is applied to give the brachytherapy applicator an unexpanded configuration (not shown), the applicator will also have an unexpanded nominal diameter (d') (not shown). The ratio of the expanded deployed nominal diameter (D) to the initial expanded nominal diameter (d), or D:d, may be representative of how effectively the brachytherapy applicator may be expanded to provide, e.g., positioning within a particular area or spacing from healthy/normal tissues. Another ratio, the d:d' ratio, may quantify the degree of collapse, or be representative of how effectively the applicator may be collapsed under vacuum or active compression. The d:d' ratio may depend on applicator features such as compressibility of the elongate body (e.g., compressibility of the foam used), number of lumens within the elongate body, and thickness of the membrane. The D:d ratio may range from about 1.3:1 to about 2:1. The d:d' ratio may range from about 1.3:1 to about 3:1. For example, the d:d' ratio may be about 1.5:1 or about 2:1. Following delivery of the prescribed dose of radiation to the body tissue(s), the applicator may be deflated and/or aspirated and withdrawn from the body. Typically, the brachytherapy applicators described herein are single use per fraction or single use per patient.

Figure 5:
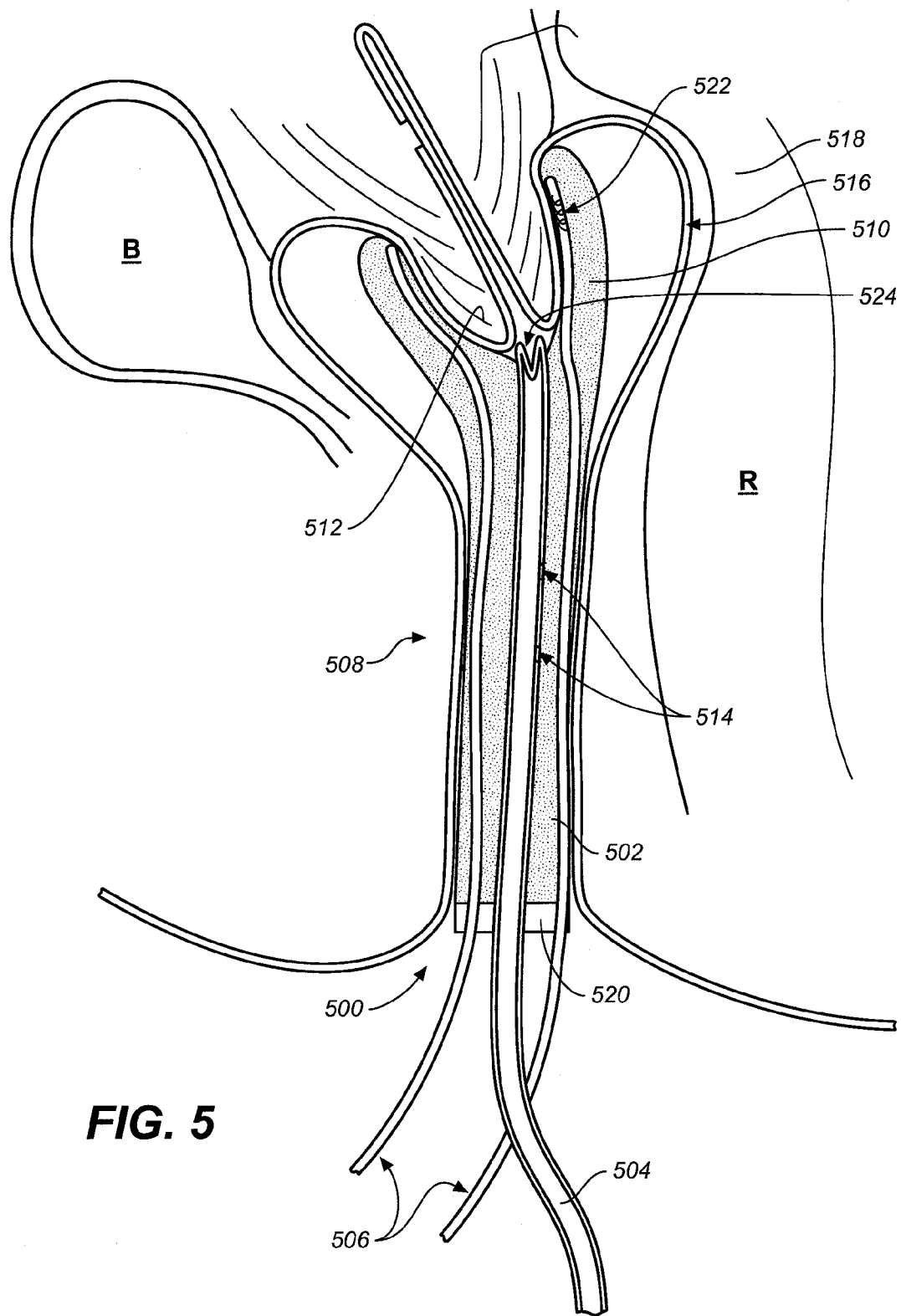
FIG. 5 depicts one variation of a brachytherapy applicator within the pelvis.

FIG. 5 shows an exemplary brachytherapy applicator for use in delivering radiation to treat gynecologic cancers. The brachytherapy applicator is depicted in its expanded deployed configuration after being positioned in situ in relation to surrounding pelvic anatomy. In FIG. 5, the brachytherapy applicator (500) has an elongate body (502), central lumen (504), additional lumens (506), and a hub (520). Although the hub (520) in FIG. 5 is shown just outside the vaginal canal (508), in other variations the hub may reside within the vaginal canal (508). Positioning the hub (520) within the vaginal canal (508) may provide improved comfort and securement of the applicator (500) within the vaginal canal (508). The elongate body (502) resides within the vaginal canal (508) and has a funnel shaped distal end (510). The funnel shape generally follows the outer contour of the cervix (512). Given that the elongate body (502) is generally made of a compliant material, e.g., foam, the funnel shaped distal end (510) is generally capable of bending off its central axis to conform to the anatomy of the area without the use of alternate-shaped applicator components that are often required when using other conventional gynecological applicators (e.g., 15 degree, 30 degree angled tandems, etc.). Expansion of the elongate body (502) via fluid flowing from a pressurized fluid source (not shown) through, in this variation, the central lumen (504) and body ports (514) may help the funnel shaped distal end (510) conform to the outer contour of the cervix (512). The membrane (516), having also been inflated by the fluid, may further expand the distal end (518) of the brachytherapy applicator (500) against the walls of the vaginal canal (508) to help secure its position therein. Once placed, inflation of the membrane (516) also spaces the bladder (B) and rectum (R) farther away from radiation sources, thereby reducing incidental dose to the bladder and rectum. A radiopaque marker (522), here a radiopaque coil, e.g., a titanium or stainless steel open-wound coil, may also be provided to help document the location of a particular lumen of the applicator. In this figure, the coil is at the distal end (510) of the applicator in the vicinity of the cervix (512). Coils of varying lengths (e.g., about 5.0 mm, about 10 mm, about 15 mm), which may be secured, e.g., by friction or an adhesive, around the distal ends of one or more of the lumens can be used to confirm the position of the lumens in the dose planning and treatment delivery processes. The coils employed may be of different lengths so that they are capable of being distinguished on CT slices, which may be used in treatment planning. For example, if the CT slice thickness used is 3.0 mm, the coils that are used should differ by more than 3.0 mm (e.g., about 5.0 mm). That way, as the dose planner or physicist views the CT slices, specific lumens may be identified and distinguished from other lumens.

In some variations, an additional lumen (closed-ended) may be positioned through the central lumen (open-ended) and distal end of the applicator into a body region, similar to how a gynecologic tandem may be positioned into the cervix or uterus. The additional lumen have a blunt or rounded tip, and may be a closed end tube that may be straight or be able to accommodate a gradual bend (e.g., about 15 degrees, or about 30 degrees, etc.) at its distal end. The type of lumen used may depend on the particular anatomy of the patient in the body region in which the applicator is being inserted. For example, in gynecologic applications, the lumen (tandem) may also have a soft tip and/or a flexible shaft body to help minimize the risk of uterine perforation during and after insertion. When a tandem (not shown) is employed in this variation, a valve (524) (e.g., a duckbill valve), as illustrated in FIG. 5, may be included in the applicator near the distal end of the central lumen (504). The valve (524) may function to seal the opening in the distal end of the central lumen (504) around the tandem when in place, or after the tandem is removed, so that fluid pressure does not dissipate during expansion of the elongate body (502) or inflation of the membrane (516), and vacuum pressure is maintained during collapse of the elongate body (502). In another variation, the additional lumen may be a catheter with distal exit holes for delivery of one or more drugs, which have been previously described. In another variation, such as the one described in FIG. 8E, the valve around the central lumen is not included, as access to the region to be aspirated or pressurized is provided through a separate lumen.

In further variations, the configuration of funnel shaped distal end (510) may be varied to help accommodate differences in patient anatomy and differences in tumor diameters and volumes. For example, the funnel may be designed to be less concave or the distal funnel diameter may be greater or less than that shown in FIG. 5. Instead of being in-line with the longitudinal axis of the applicator, the funnel portion may also be flexed or alternatively, may be pre-shaped to be variously angled from the longitudinal axis of the applicator, e.g., the angle between the main axis of the funnel and the longitudinal axis of the applicator may be anywhere between 0 degrees to about 90 degrees. The funnel shaped applicator may also be useful in clinical situations where the target tissue to be irradiated (e.g., a tumor) can be isolated and have a diameter of about 2.0 to about 5.0 cm.

IV. Other Spacing Devices

As previously mentioned, spacing healthy or normal tissues from radiation sources may reduce the dose of radiation delivered to those tissues, which in turn may help to reduce the complications associated with radiation therapy. With this in mind, one or more inflatable spacers may be used to space healthy/normal tissues from the radiation source, with or without concurrent radiation treatment with the brachytherapy applicators herein described. For example, the inflatable spacers may be used during treatment with external beam radiation.

The inflatable spacers may be of any suitable configuration. For example, they may be of any suitable size, geometry, or volume. For gynecological applications, the inflatable spacers may include an inflatable member that is attached to a catheter. In its inflated state, the inflatable member may have dimensions between about 5.0 cm to about 12 cm in length, about 2.0 cm to about 8.0 cm in width, and about 0.5 cm to about 3.0 cm thick. In general, the inflatable members are configured to conform to adjacent tissue surfaces. The inflatable members may be made from any distensible material, including, but not limited to, fluoropolymers, natural and synthetic latex, polyurethane, silicone, thermoplastic elastomers, and the like. Further, the inflatable members may incorporate a radiographically detectable material, e.g., in the inflation fluid, to help determine position and/or degree of inflation, etc. Additionally, radiopaque materials such as contrast iodine, or other fluid suspensions containing radiodense salts (e.g., barium sulfate) may be infused into the inflatable members to provide an additional radiation-attenuation effect, if desired. The inflatable spacers may be configured so that the degree of inflation can be adjusted.

When used in gynecologic applications, the inflatable spacers may be placed at the time of hysterectomy in their deflated state, either between the rectum and vaginal wall or between the bladder and vaginal wall, or both. During dose delivery the inflatable members are then inflated. Between dose fractions the inflatable members may be deflated.

In addition to providing a space between the radiation source and the bladder/rectum, the inflatable spacers may be used to displace the small bowel from the pelvic area. The inflatable spacers may be configured for placement via open surgery or via a minimally invasive approach, e.g., via a laparoscopic procedure. In some variations, the inflatable spacers may include a drainage lumen so that they may function as both a postoperative drain and a spacer.

In one variation, as illustrated in FIGS. 6A-6C, the inflatable spacer (600) includes a catheter (602) having a proximal end (604), a distal end (606), and catheter lumen (620) (shown in FIGS. 6B and 6C) extending therethrough. The catheter lumen (620) may also include a drainage lumen (622) and an inflation lumen (624). An inflatable member, balloon (608), is attached to the distal end (606). The balloon (608) in FIG. 6A is shown with multiple inflatable channels (610), but it should be understood that other balloon or inflatable member configurations may also be employed. When a drainage lumen (622) is included, drainage openings (618) may also be provided in the wall of catheter (602) and configured to be in fluid communication with drainage lumen (622). Further, a removable stylet (626) may be advanced within the drainage lumen (622) to facilitate placement of the inflatable spacer (600).

To form the inflatable channels (610), portions of the wall of balloon (608) may be longitudinally adhered to each other to form flexible regions (612) by techniques well known in the art (e.g., RF and resistance bonding, welding, adhesive bonding, etc.). The flexible regions (612) may partially or completely extend across the length of the balloon (608). Referring to the transverse cross-sectional view of balloon (608) provided in FIG. 6B and FIG. 6C, it is shown how the flexible regions (612) may function as hinges or provide areas of increased flexibility/bendability that help the balloon (608) to conform to the outer surface (614) of a tissue (616) when inflated. Any fluid may be used to inflate the balloon (608). For example, a gas such air may be used, or any biocompatible liquid or suspension, including fluids containing radiographically detectable material, as previously described, may be employed. The fluid may be infused from a port (628) at the proximal end (604) of the catheter (602) through inflation lumen (624) into balloon (608).

The invention claimed is:

1. A gynecological brachytherapy applicator comprising:
   a porous and compliant matrix in the form of a substantially cylindrical conformable elongate body having a proximal end and a distal end,
   a central catheter at least partially received in the porous and compliant matrix, and at least one pair of opposed peripheral catheters at least partially received in the porous and compliant matrix;
   wherein the maximum distance between the at least one pair of opposed peripheral catheters being in a range from 70% to equal to or smaller than 100% of the outer diameter of the elongate body, wherein the elongate body has an initial expanded configuration, an unexpanded configuration for advancement of the applicator to a target tissue, and an expanded deployed configuration, wherein the conformable elongate body is imageable by computed tomography,
   wherein the elongate body provides a collapsible and expandable matrix of support such that a position and spacing of the central catheter relative to the at least one pair of opposed peripheral catheters within the porous and compliant matrix are stabilized in the expanded deployed configuration and the initial expanded configuration, and wherein the elongate body is made of a material comprising a foam.

2. The gynecological brachytherapy applicator of claim 1, wherein the maximum distance between the at least one pair of opposed peripheral catheters is at least about 72% of the outer diameter of the elongate body.

3. The gynecological brachytherapy applicator of claim 1, wherein the maximum distance between the at least one pair of opposed peripheral catheters is at least about 75% of the outer diameter of the elongate body.

4. The gynecological brachytherapy applicator of claim 1, wherein the maximum distance between the at least one pair of opposed peripheral catheters is at least about 80% of the outer diameter of the elongate body.

5. The gynecological brachytherapy applicator of claim 1, wherein the maximum distance between the at least one pair of opposed peripheral catheters is at least about 85% of the outer diameter of the elongate body.

6. The gynecological brachytherapy applicator of claim 1, wherein the maximum distance between the at least one pair of opposed peripheral catheters is at least about 90% of the outer diameter of the elongate body.

7. The gynecological brachytherapy applicator of claim 1, wherein the applicator contains at least two pairs of opposed peripheral catheters at least partially received in the porous and compliant matrix.

8. The gynecological brachytherapy applicator of claim 1, wherein the applicator contains at least three pairs of opposed peripheral catheters at least partially received in the porous and compliant matrix.

9. The gynecological brachytherapy applicator of claim 1, wherein the elongate body is constructed from a material comprising a compliant material.

10. The gynecological brachytherapy applicator of claim 1, wherein the foam comprises an open cell foam.

11. The gynecological brachytherapy applicator of claim 1, wherein the foam is selected from the group consisting of polyester foam, polyurethane foam, silicone foam, thermoplastic elastomer foam, and combinations thereof.

12. The gynecological brachytherapy applicator of claim 11, wherein the foam comprises a polyurethane foam.

13. The gynecological brachytherapy applicator of claim 1, wherein the distal end comprises a central opening in communication with the central catheter for advancement of a tandem therethrough.

14. The gynecological brachytherapy applicator of claim 13, wherein the tandem comprises a radiation source.

15. The gynecological brachytherapy applicator of claim 1, wherein the distal end of the elongate body is rounded.

16. The gynecological brachytherapy applicator of claim 1, wherein the distal end of the elongate body is flat.

17. The gynecological brachytherapy applicator of claim 1, wherein the distal end of the elongate body is funnel shaped.

18. The gynecological brachytherapy applicator of claim 1, wherein at least portions of the at least one pair of opposed peripheral catheters are oriented substantially parallel to the longitudinal axis of the elongate body.

19. The gynecological brachytherapy applicator of claim 1, wherein the at least one pair of opposed peripheral catheters is symmetrically spaced around the circumference of the elongate body.

20. The gynecological brachytherapy applicator of claim 1, wherein the at least one pair of opposed peripheral catheters is asymmetrically spaced around the circumference of the elongate body.

21. The gynecological brachytherapy applicator of claim 1, further comprising a membrane surrounding the elongate body.

22. The gynecological brachytherapy applicator of claim 21, wherein the membrane comprises a polymeric material.

23. The gynecological brachytherapy applicator of claim 22, wherein the polymeric material is selected from the group consisting of fluoropolymers, natural and synthetic latex, polyurethane, silicone, and combinations thereof.

24. The gynecological brachytherapy applicator of claim 21, wherein the membrane is inflatable around a portion of the elongate body.

25. The gynecological brachytherapy applicator of claim 21, wherein one or more of the membrane, central catheter, at least one peripheral catheter, and elongate body, or portions thereof, are radiopaque, or combinations thereof are radiopaque.

26. The gynecological brachytherapy applicator of claim 1, wherein the elongate body has an initial expanded diameter, an unexpanded diameter, and an expanded deployed diameter.

27. The gynecological brachytherapy applicator of claim 26, wherein the ratio of the expanded deployed to the initial expanded diameters is between 1.3:1 to about 2:1.

28. The gynecological brachytherapy applicator of claim 26, wherein the ratio of the initial expanded to unexpanded diameters is between 1.3:1 to about 3:1.

29. The gynecological brachytherapy applicator of claim 1, wherein the distal end of the elongate body in its initial deployed configuration or expanded deployed configuration is conformable to one or more gynecological tissue surfaces.

30. The gynecological brachytherapy applicator of claim 29, wherein the one or more gynecological tissue surfaces comprises at least one tissue surface of the cervix.

31. The gynecological brachytherapy applicator of claim 1, wherein the elongate body in its expanded deployed configuration is configured to secure the applicator within the vaginal canal or against the cervix.

32. The gynecological brachytherapy applicator of claim 1, further comprising a radiation source within the central catheter, at least one peripheral catheter of the at least one pair of opposed peripheral catheters, or a combination thereof.

33. The gynecological brachytherapy applicator of claim 32, wherein the radiation source comprises a radioactive liquid, an x-ray source, a radiation seed, or combinations thereof.

34. The gynecological brachytherapy applicator of claim 32, wherein the radiation source comprises radionuclides selected from the group consisting of cesium, iridium, iodine, cobalt, palladium, strontium, yttrium, gold, ruthenium, californium, and combinations thereof.

35. The gynecological brachytherapy applicator of claim 34, wherein the radiation source comprises iridium.

36. The gynecological brachytherapy applicator of claim 1 further comprising a layer of noncompressible material coupling the at least one peripheral catheter to an outer surface of the elongate body.

37. The gynecological brachytherapy applicator of claim 1 wherein the elongate body comprises a unitary piece of a compliant material.

38. The gynecological brachytherapy applicator of claim 1 wherein the elongate body is made of a material comprising a foam, and the foam is configured to be expandable and collapsible by infusing and withdrawing an inflation medium into and from the foam.

* * * * *